US010792431B2

(12) United States Patent
Duinat et al.

(10) Patent No.: US 10,792,431 B2
(45) Date of Patent: *Oct. 6, 2020

(54) SYRINGE PACKAGING SYSTEM

(71) Applicant: Fresenius Kabi Deutschland GmbH, Bad Homburg (DE)

(72) Inventors: Brigitte Duinat, Grenoble (FR); Charles D. Shermer, Raleigh, NC (US); Luc Dorelon, St. Martin de la Cluze (FR)

(73) Assignee: Fresenius Kabi Deustchland GmbH, Bad Homburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/057,279

(22) Filed: Aug. 7, 2018

(65) Prior Publication Data
US 2018/0344936 A1 Dec. 6, 2018

Related U.S. Application Data

(63) Continuation of application No. 15/206,029, filed on Jul. 8, 2016, now Pat. No. 10,064,998.
(Continued)

(51) Int. Cl.
*A61M 5/31* (2006.01)
*A61M 5/315* (2006.01)
(Continued)

(52) U.S. Cl.
CPC .......... *A61M 5/3137* (2013.01); *A61M 5/002* (2013.01); *A61M 5/31505* (2013.01);
(Continued)

(58) Field of Classification Search
CPC ........ A61M 5/00; A61M 5/002; A61M 5/178; A61M 5/31; A61M 5/3137; A61M 5/315;
(Continued)

(56) References Cited

U.S. PATENT DOCUMENTS 3,342,319 A  9/1967 Faulseit
4,671,408 A  6/1987 Raines et al.
(Continued)

FOREIGN PATENT DOCUMENTS

WO  WO 2001/023017 A2  4/2001
WO  WO 2006/018626 A1  2/2006

OTHER PUBLICATIONS

European Patent Office, International Search Report in International Application No. PCT/IB2016/054126 (dated Sep. 26, 2016).
(Continued)

*Primary Examiner* — Bryon P Gehman
(74) *Attorney, Agent, or Firm* — Leydig, Voit & Mayer, Ltd.

(57) ABSTRACT

A syringe packaging system that includes a tube and a cap for enclosing a pre-filled syringe is disclosed. The tube includes a tube cut flange and the cap includes a cut skirt. With a syringe barrel contained within the tube, a syringe barrel cut flange is aligned with the tube cut flange. With the pre-filled syringe enclosed within the tube and the cap, the cut skirt of the cap surrounds the syringe barrel cut flange. In one embodiment, a film is securable to a portion of the tube and a portion of the cap to connect the tube and the cap with the pre-filled syringe enclosed within the cap and the tube.

17 Claims, 30 Drawing Sheets

Related U.S. Application Data

(60) Provisional application No. 62/191,052, filed on Jul. 10, 2015.

(51) Int. Cl.
*A61M 5/32* (2006.01)
*A61M 5/00* (2006.01)

(52) U.S. Cl.
CPC ... *A61M 5/3202* (2013.01); *A61M 2005/3104* (2013.01); *A61M 2005/3142* (2013.01)

(58) Field of Classification Search
CPC .. A61M 5/31505; A61M 5/32; A61M 5/3202; A61M 5/50; A61M 2005/3104; A61M 2005/3142
USPC .................................................. 206/364, 365
See application file for complete search history.

(56) References Cited

U.S. PATENT DOCUMENTS

| | | | |
|---|---|---|---|
| 4,877,132 A | 10/1989 | Makris et al. | |
| 4,979,616 A | 12/1990 | Clanton | |
| 5,417,326 A | 5/1995 | Winer | |
| 5,519,931 A | 5/1996 | Reich | |
| 5,566,828 A | 10/1996 | Claes et al. | |
| 5,615,772 A | 4/1997 | Naganuma | |
| 6,073,759 A | 6/2000 | Lalmborne et al. | |
| 6,368,305 B1 | 4/2002 | Dutton | |
| 6,595,362 B2 | 7/2003 | Penney et al. | |
| 6,808,507 B2 * | 10/2004 | Roser ................. | A61M 5/31511 604/110 |
| 6,929,126 B1 | 8/2005 | Herbert | |
| 7,597,196 B2 | 10/2009 | Langone | |
| 7,875,007 B2 | 1/2011 | Perot et al. | |
| 8,043,267 B2 | 10/2011 | Nanba et al. | |
| 9,144,465 B2 | 9/2015 | Hunkeler et al. | |
| 9,333,146 B2 | 5/2016 | Perot et al. | |
| 9,333,288 B2 | 5/2016 | Hilliard et al. | |
| 9,333,289 B1 | 5/2016 | Hirschmann et al. | |
| 10,052,437 B2 | 8/2018 | Duinat et al. | |
| 10,064,998 B2 | 9/2018 | Duinat et al. | |
| 10,159,796 B2 * | 12/2018 | Schiff ................. | A61M 5/31511 |
| 10,220,150 B2 | 3/2019 | Ito et al. | |
| 10,525,209 B2 | 1/2020 | Matsui | |
| 2004/0069667 A1 | 4/2004 | Tomellini et al. | |
| 2011/0087173 A1 | 4/2011 | Sibbitt, Jr. et al. | |
| 2013/0081974 A1 | 4/2013 | Hilliard et al. | |
| 2013/0082057 A1 | 4/2013 | Schiff et al. | |
| 2014/0078854 A1 | 3/2014 | Head et al. | |
| 2017/0007770 A1 | 1/2017 | Duinat et al. | |
| 2017/0007771 A1 | 1/2017 | Duinat et al. | |
| 2018/0126065 A1 | 5/2018 | Duinat et al. | |
| 2018/0344938 A1 | 12/2018 | Duinat et al. | |

OTHER PUBLICATIONS

European Patent Office, Written Opinion in International Application No. PCT/IB2016/054126 (dated Sep. 26, 2016).

* cited by examiner

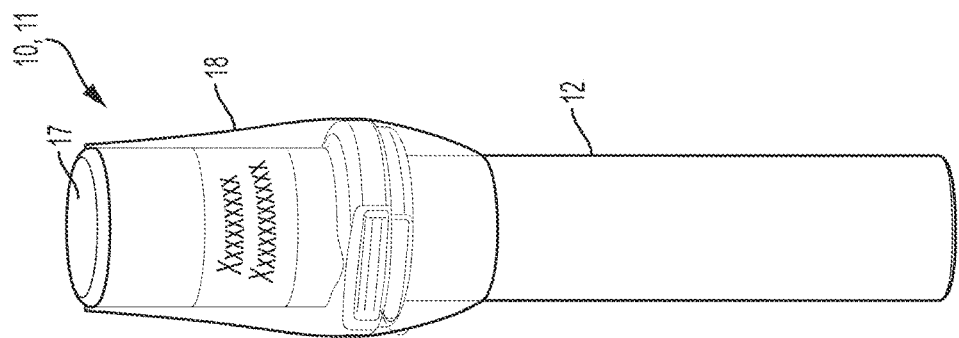
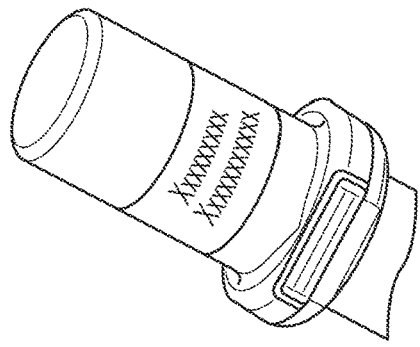
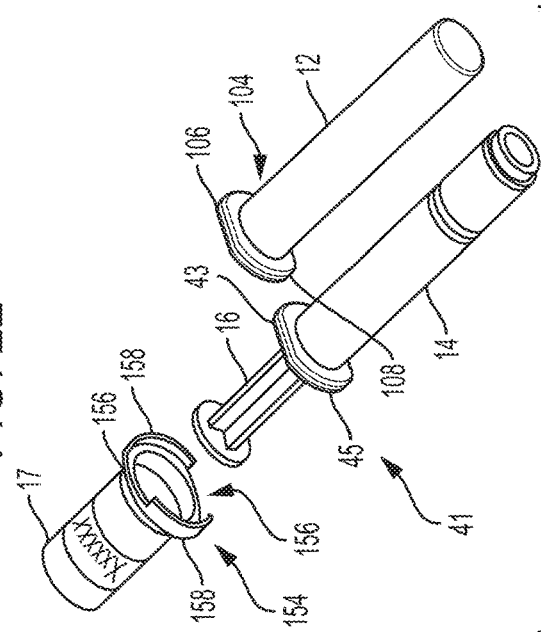
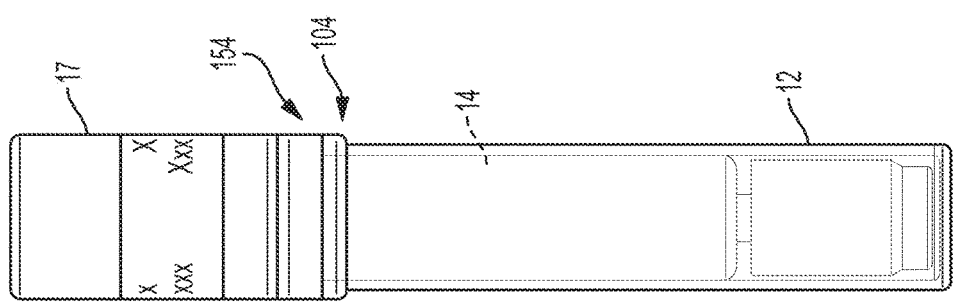
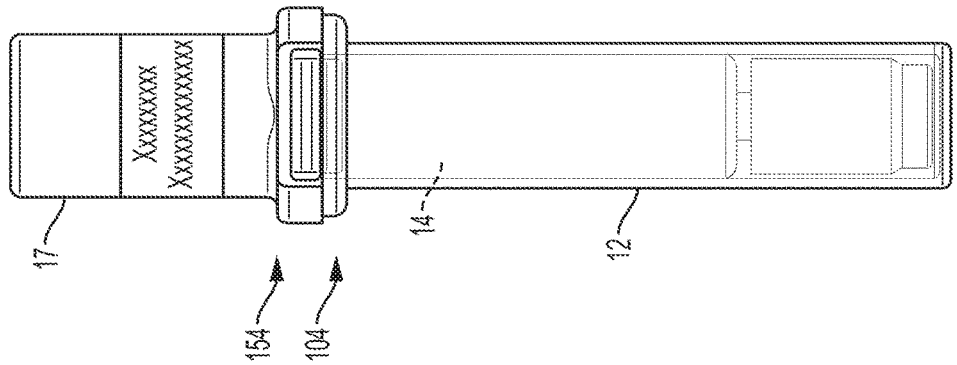
FIG. 24
FIG. 22
FIG. 23
FIG. 21
FIG. 20

SYRINGE PACKAGING SYSTEM

CROSS-REFERENCE TO RELATED APPLICATIONS

This patent application is a continuation of U.S. patent application Ser. No. 15/206,029, filed Jul. 8, 2016, which claims the benefit of U.S. Provisional Application No. 62/191,052, filed Jul. 10, 2015, which is incorporated herein by reference in its entirety.

BACKGROUND OF THE INVENTION

Field of the Disclosure

The present disclosure relates generally to a syringe assembly adapted for delivery of a fluid. More particularly, the present disclosure relates to a syringe packaging system that allows for reduced storage space of a syringe assembly.

Description of the Related Art

Syringe assemblies, and in particular hypodermic syringes, are well known in the medical field for dispensing fluids, such as medications. A conventional syringe typically includes a syringe barrel with an opening at one end and a plunger mechanism disposed through the opposite end. The plunger mechanism typically includes a plunger rod extending through the barrel, with a plunger head or stopper disposed at the end of the plunger rod within the syringe barrel, and with a finger flange at the other end of the plunger rod extending out of the syringe barrel. In use, the plunger rod is retracted through the syringe barrel to aspirate or fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the syringe barrel for attachment with a fluid line of a patient. Upon application of a force to depress the plunger rod and stopper through the syringe barrel towards the front end of the syringe barrel, the contents of the syringe are thereby forced out of the syringe barrel through the opening at the front end for delivery to the patient.

Commonly, hypodermic syringes may be packaged as "pre-filled" devices, wherein the syringe is pre-filled with medication prior to being packaged and delivered to the patient. In this manner, the need for the user to fill the device prior to injection is eliminated, thereby saving time and maintaining consistent volumes for delivery.

However, packaging of such pre-filled syringes tends to be bulky and difficult to ship and store. Pre-filled syringes and pre-filled metered dose syringes are often filled with fluids, such as a medication, at a production facility, packaged, and then shipped to a medical facility. Once at the facility, these syringes are often placed in controlled storage and/or locked cabinets to reduce theft of the syringes themselves and/or of the contents of these syringes. The space within these controlled storage locations is often limited, thus there is a need for a syringe assembly that has a smaller packaging footprint to reduce the amount of storage space required for containing the syringe.

SUMMARY OF THE INVENTION

In accordance with an embodiment of the present invention, a syringe packaging system includes a tube and a cap for enclosing a pre-filled syringe. The tube includes a tube cut flange and the cap includes a cut skirt. With a syringe barrel contained within the tube, a syringe barrel cut flange is aligned with the tube cut flange. With the pre-filled syringe enclosed within the tube and the cap, the cut skirt of the cap surrounds the syringe barrel cut flange. In one embodiment, a film is securable to a portion of the tube and a portion of the cap to connect the tube and the cap with the pre-filled syringe enclosed within the cap and the tube.

In accordance with an embodiment of the present invention, a syringe packaging system includes a pre-filled syringe including a syringe barrel having a proximal end, a distal end, and a sidewall extending therebetween and defining a chamber, the proximal end having a syringe barrel cut flange; and a packaging member enclosing the pre-filled syringe, the packaging member including a tube having a proximal end and a distal end, the proximal end including a tube cut flange, with the syringe barrel contained within the tube, the syringe barrel cut flange is aligned with the tube cut flange.

In one configuration, the syringe barrel cut flange includes a first flat wall portion and a first arcuate wall portion. In another configuration, the tube cut flange includes a second flat wall portion and a second arcuate wall portion. In yet another configuration, the syringe packaging system includes a cap having a first end and a second end, the second end including a cut skirt. In one configuration, the cut skirt includes a third flat wall portion and a third arcuate wall portion. In another configuration, with the pre-filled syringe enclosed within the packaging member, the cut skirt of the cap surrounds the syringe barrel cut flange. In yet another configuration, the syringe packaging system includes a film securable to a portion of the tube and a portion of the cap to connect the tube and the cap with the pre-filled syringe enclosed within the cap and the tube. In one configuration, the distal end of the tube is closed.

In accordance with another embodiment of the present invention, a syringe packaging system includes a pre-filled syringe, comprising: a syringe barrel having a proximal end, a distal end, and a sidewall extending therebetween and defining a chamber, the proximal end having a syringe barrel cut flange; a fluid disposed within the chamber of the syringe barrel; a stopper slidably disposed within the chamber of the syringe barrel; and a plunger rod having a proximal end and a distal end engageable with a portion of the stopper; and a packaging member enclosing the pre-filled syringe, the packaging member comprising: a tube having a proximal end and a distal end, the proximal end including a tube cut flange; a cap having a first end and a second end, the second end including a cut skirt; and a film securable to a portion of the tube and a portion of the cap to connect the tube and the cap with the pre-filled syringe enclosed within the cap and the tube.

In one configuration, the syringe barrel cut flange includes a first flat wall portion and a first arcuate wall portion. In another configuration, the tube cut flange includes a second flat wall portion and a second arcuate wall portion. In yet another configuration, the cut skirt includes a third flat wall portion and a third arcuate wall portion. In one configuration, with the pre-filled syringe enclosed within the packaging member, the cut skirt of the cap surrounds the syringe barrel cut flange. In another configuration, with the syringe barrel contained within the tube, the syringe barrel cut flange is aligned with the tube cut flange. In yet another configuration, the distal end of the tube is closed.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 20 is an elevation view of a syringe packaging system in accordance with an embodiment of the present invention.

FIG. 21 is an elevation view of a syringe packaging system in accordance with an embodiment of the present invention.

FIG. 22 is a perspective view of a proximal end of a syringe packaging system in accordance with an embodiment of the present invention.

FIG. 23 is an exploded, perspective view of a syringe packaging system in accordance with an embodiment of the present invention.

FIG. 24 is an assembled, perspective view of a syringe packaging system in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
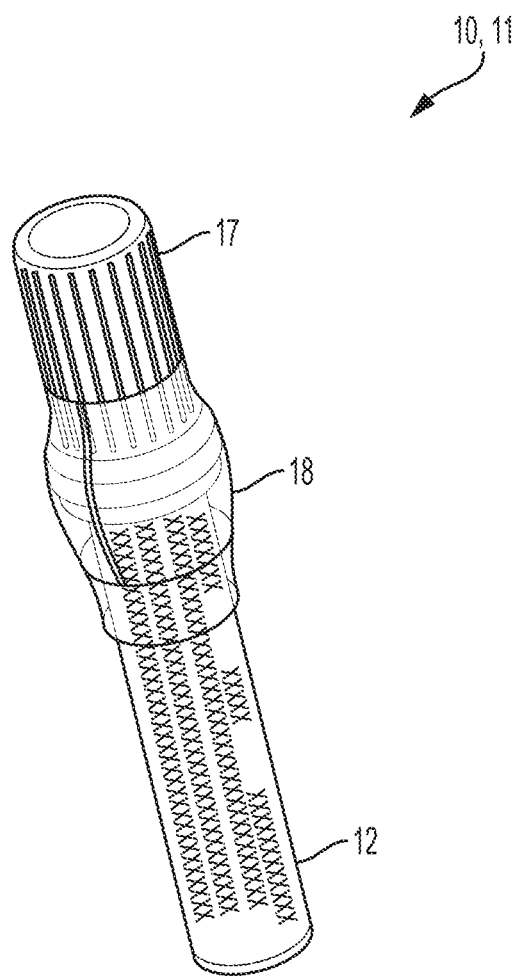
FIG. 1 is a perspective view of a syringe packaging system in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a direction generally toward an end of a syringe or a syringe assembly adapted for contact with a patient and/or engagement with a separate device such as a needle assembly or IV connection assembly, and "proximal" refers to the opposite direction of distal, i.e., away from the end of a syringe or a syringe assembly adapted for engagement with the separate device. For purposes of this disclosure, the above-mentioned references are used in the description of the components of a syringe or a syringe assembly in accordance with the present disclosure.

FIGS. 1-39 illustrate exemplary embodiments of the present disclosure. Referring to FIGS. 1-39, a syringe packaging system 10 includes a packaging member or packaging assembly 11 having a tube 12, a cap 17, and a film 18; and a syringe or a syringe assembly 13 including a syringe barrel 14, a plunger rod 16, and a stopper 19. The tube 12 and cap 17 of the syringe packaging system 10 provides a packaging member for a pre-filled syringe, such as syringe 13. The tube 12 and cap 17 of the present disclosure allows for reduced storage space of a pre-filled syringe. For example, the tube 12 and cap 17 allows for reduced storage space of a pre-filled syringe in an automated dispensing cabinet.

Figure 15:
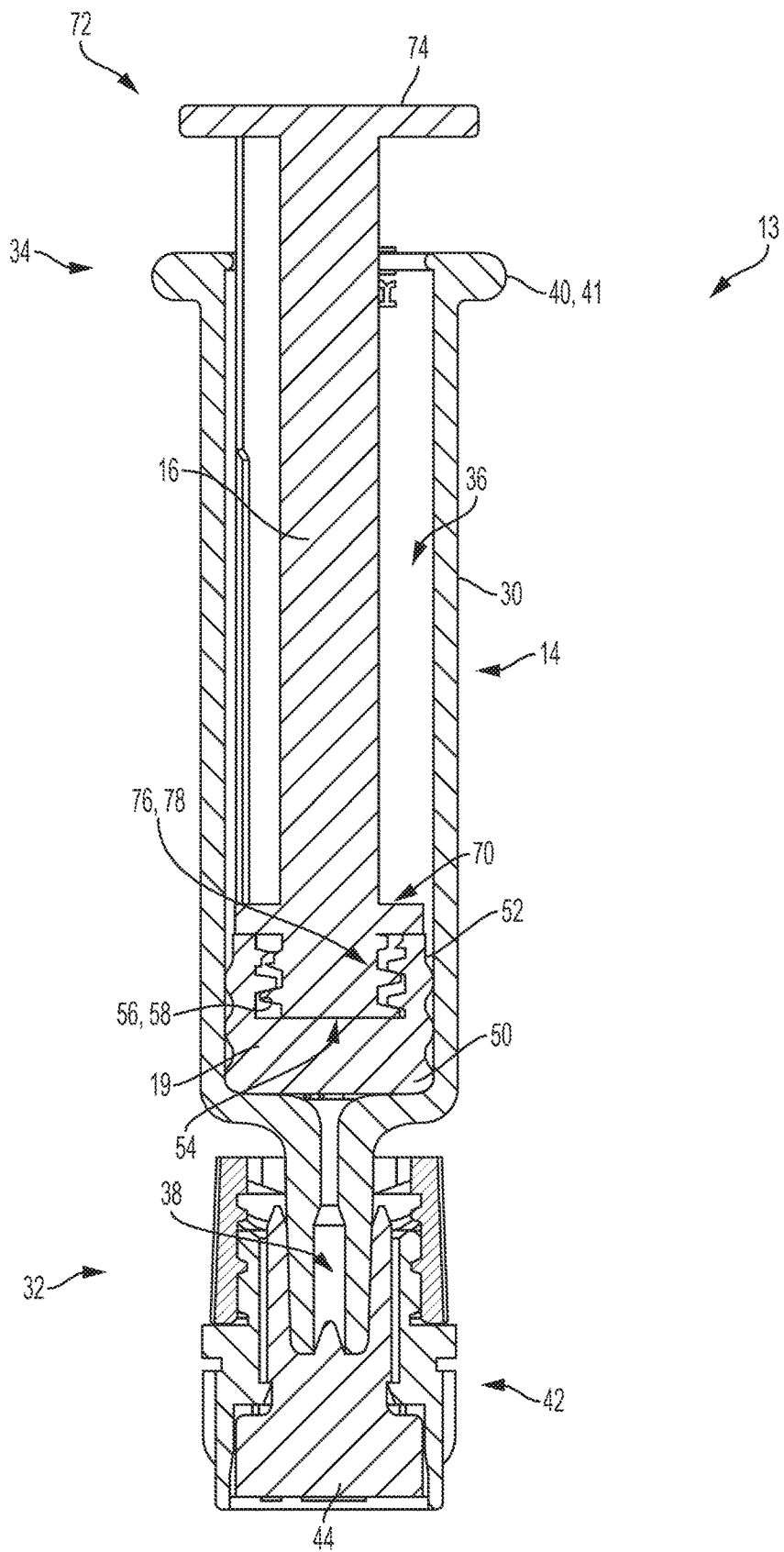
FIG. 15 is a cross-sectional view of a syringe in a first position in accordance with an embodiment of the present invention.
Figure 16:
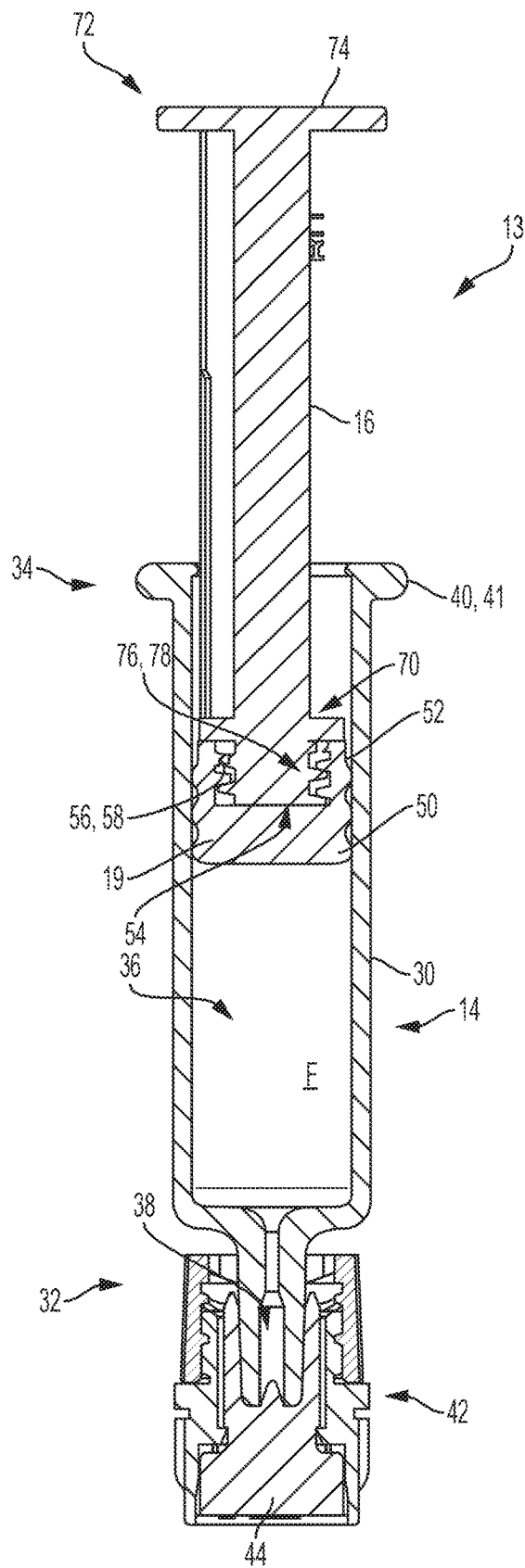
FIG. 16 is a cross-sectional view of a syringe in a second position in accordance with an embodiment of the present invention.

Referring to FIGS. 15 and 16, in one embodiment, syringe assembly 13 includes syringe barrel 14, plunger rod 16, and a stopper 19. Syringe assembly 13 may be adapted for dispensing and delivery of a fluid and/or collection of a fluid. For example, syringe assembly 13 may be used for injection or infusion of fluid such as a medication or drug into a patient. Syringe assembly 13 is contemplated for use in connection with a needle, such as by connecting syringe assembly 13 to a separate needle assembly (not shown), or alternatively for connection with an intravenous (IV) connection assembly (not shown). It can be appreciated that the present disclosure can be used with any type of syringe assembly, particularly those which are placed in a controlled storage environment in which storage space is limited. These types of syringes include traditional pre-filled syringe assemblies, metered dose syringes, aspiration syringes for withdrawing fluid from a patient or medication from a container, and the like.

In one embodiment, the tube 12 and cap 17 can be designed for a syringe 13 that is a cut flange syringe. In other embodiments, the tube 12 and cap 17 can be designed for a syringe 13 that is a round flange syringe. In other embodiments, the tube 12 and cap 17 can be designed for other syringes.

Figure 17:
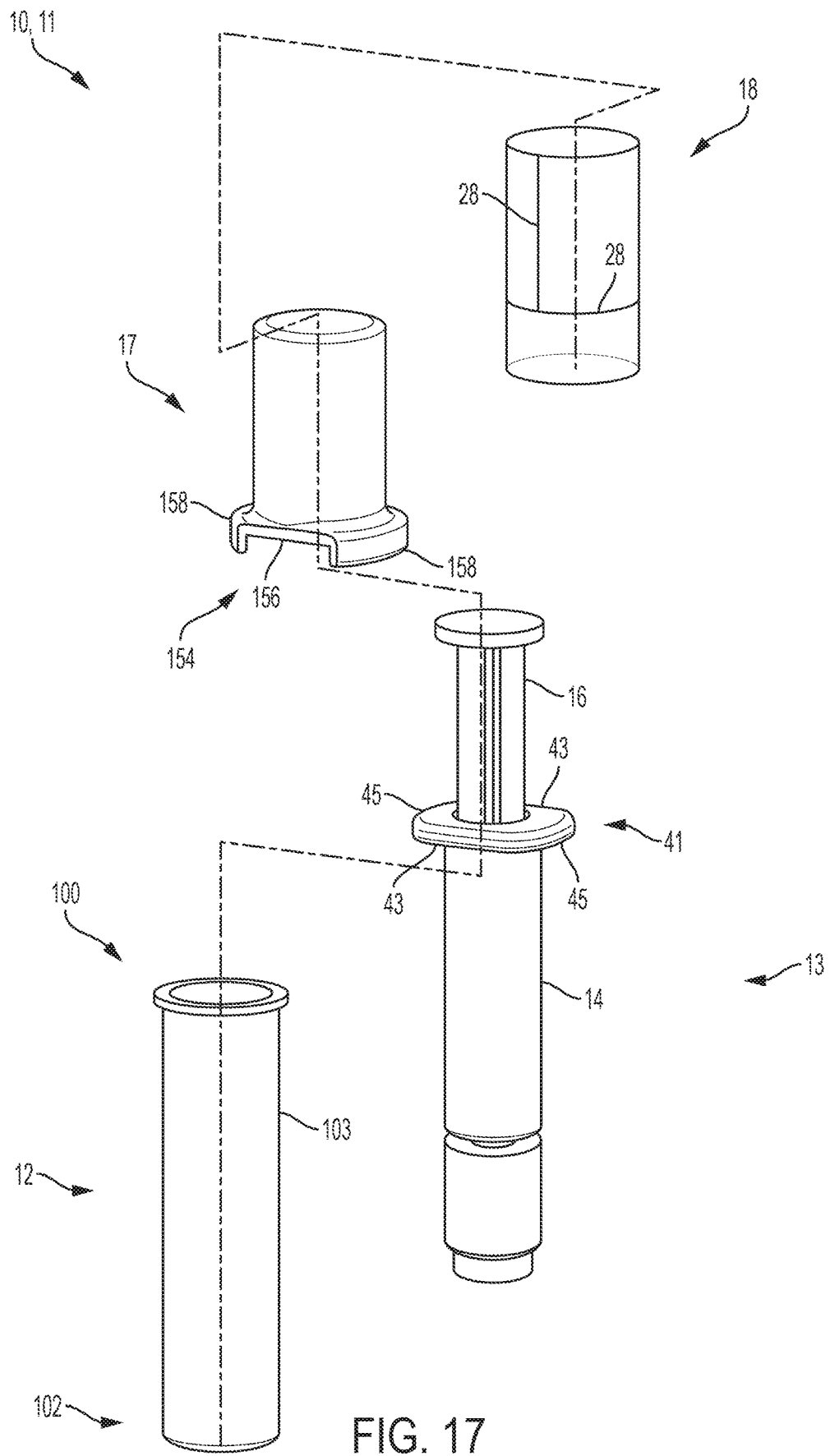
FIG. 17 is an exploded, perspective view of a syringe packaging system in accordance with an embodiment of the present invention.
Figure 18:
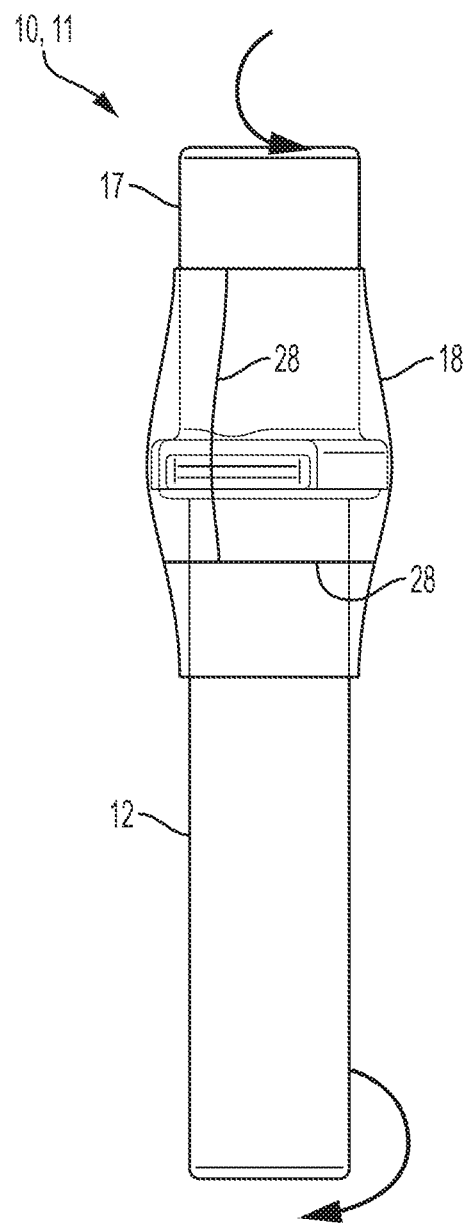
FIG. 18 is an assembled, front view of the syringe packaging system of FIG. 17, with a film connecting a tube and a cap in accordance with an embodiment of the present invention.
Figure 19:
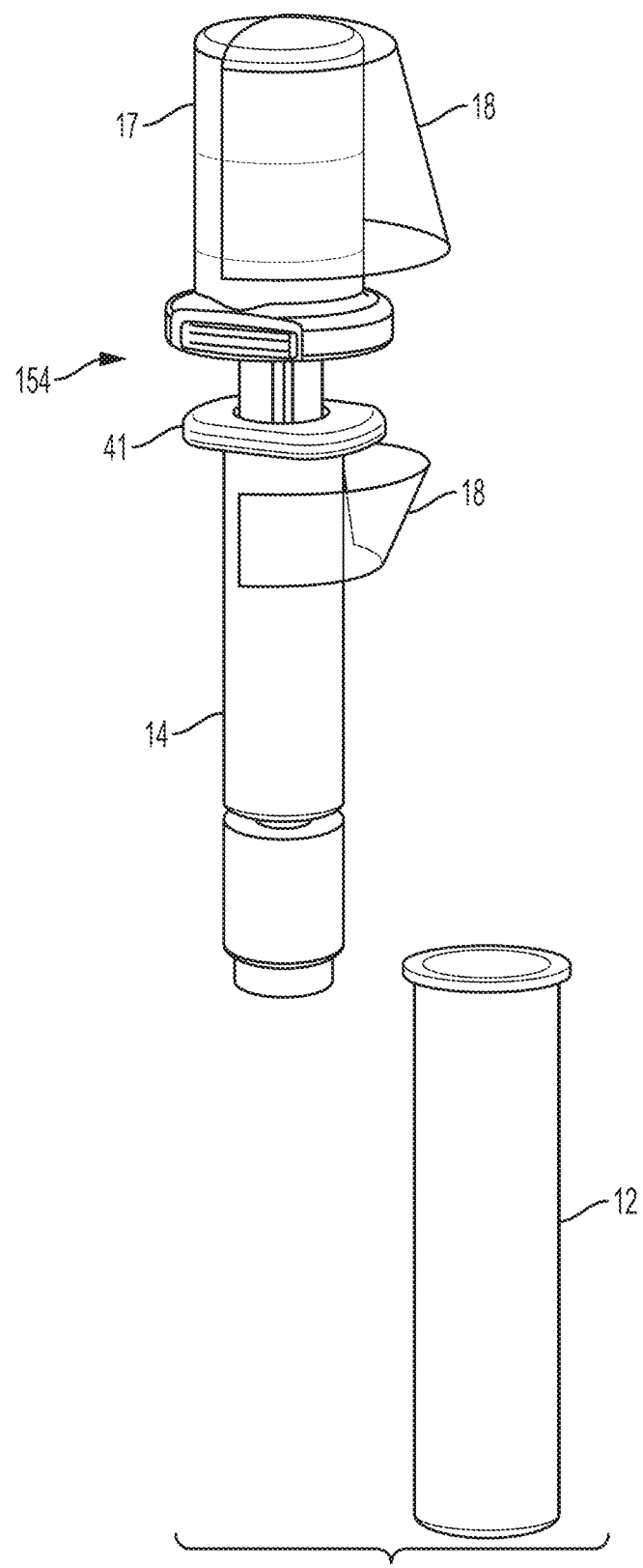
FIG. 19 is a perspective view of a syringe packaging system, with a film opened and a syringe removed from a tube in accordance with an embodiment of the present invention.
Figure 25:
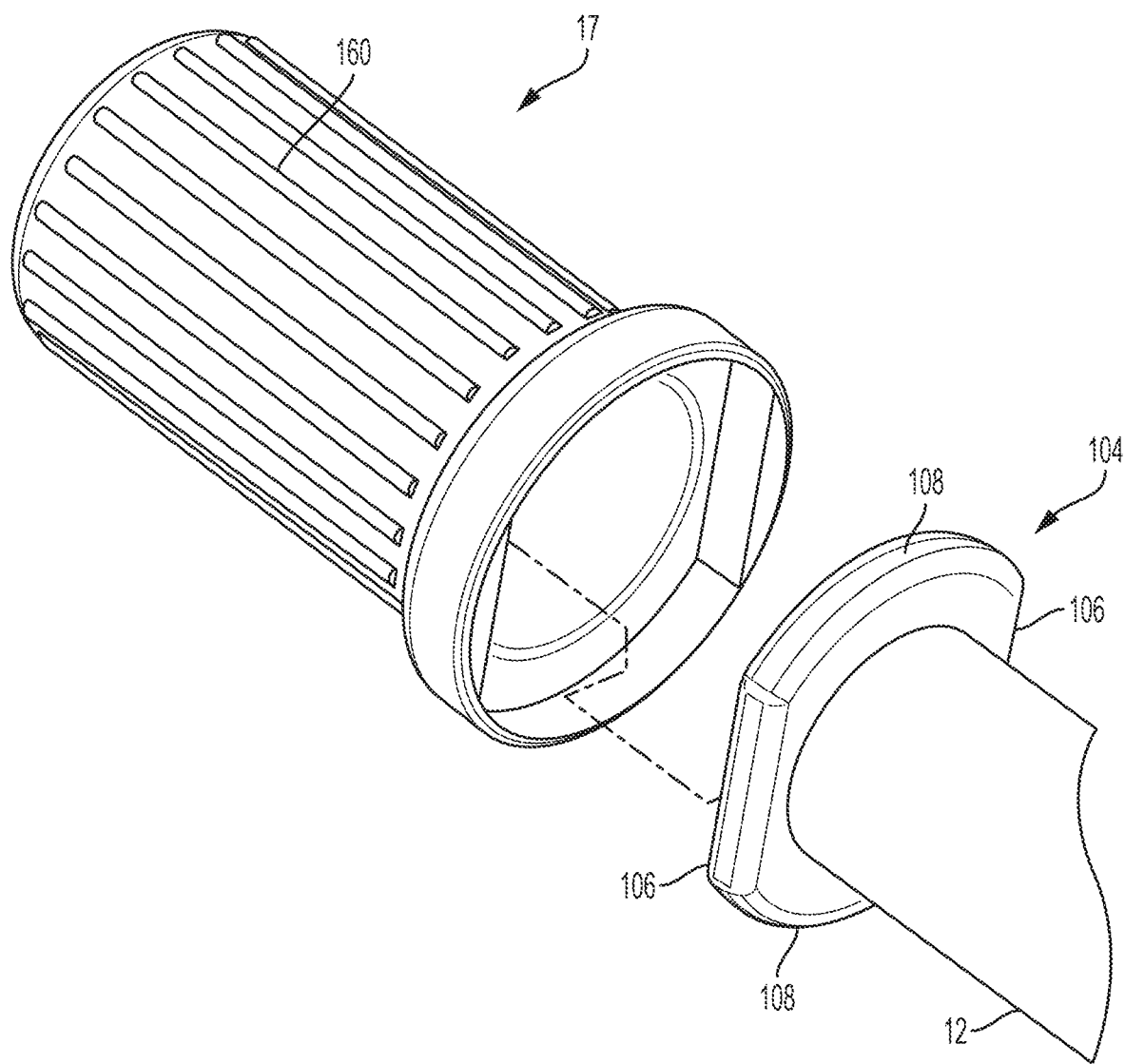
FIG. 25 is an exploded, perspective view of a cap and a tube in accordance with an embodiment of the present invention.
Figure 26:
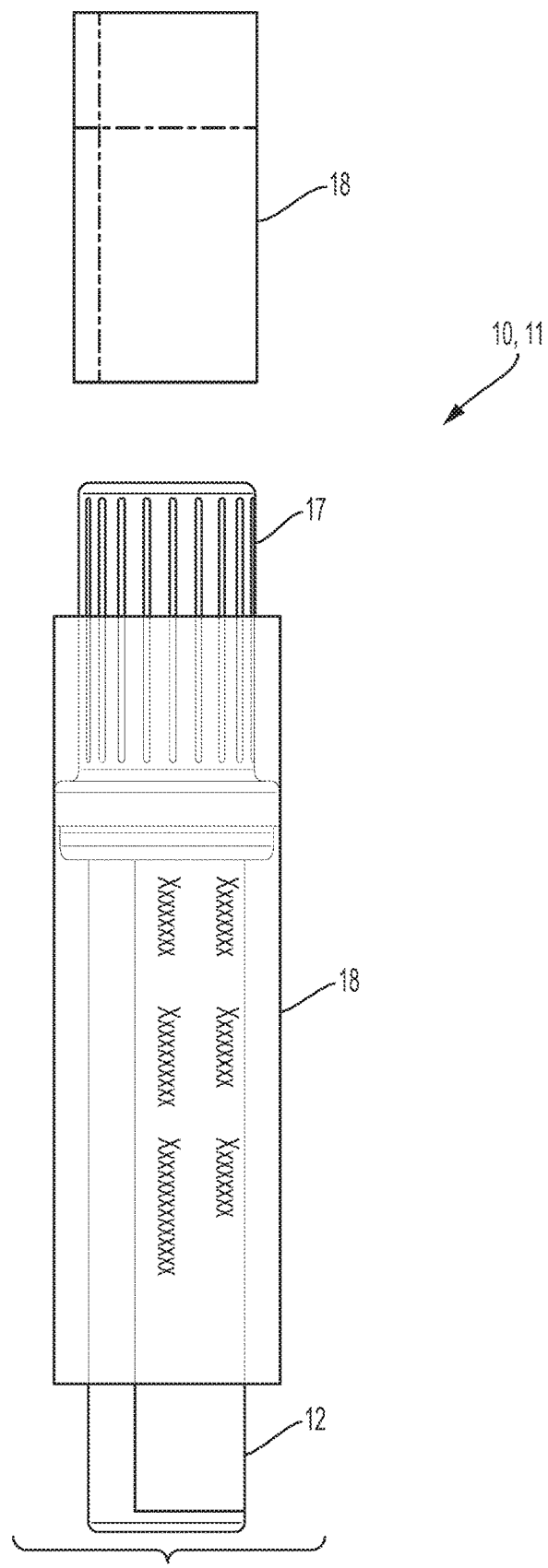
FIG. 26 is a front view of a syringe packaging system in accordance with an embodiment of the present invention.
Figure 27:
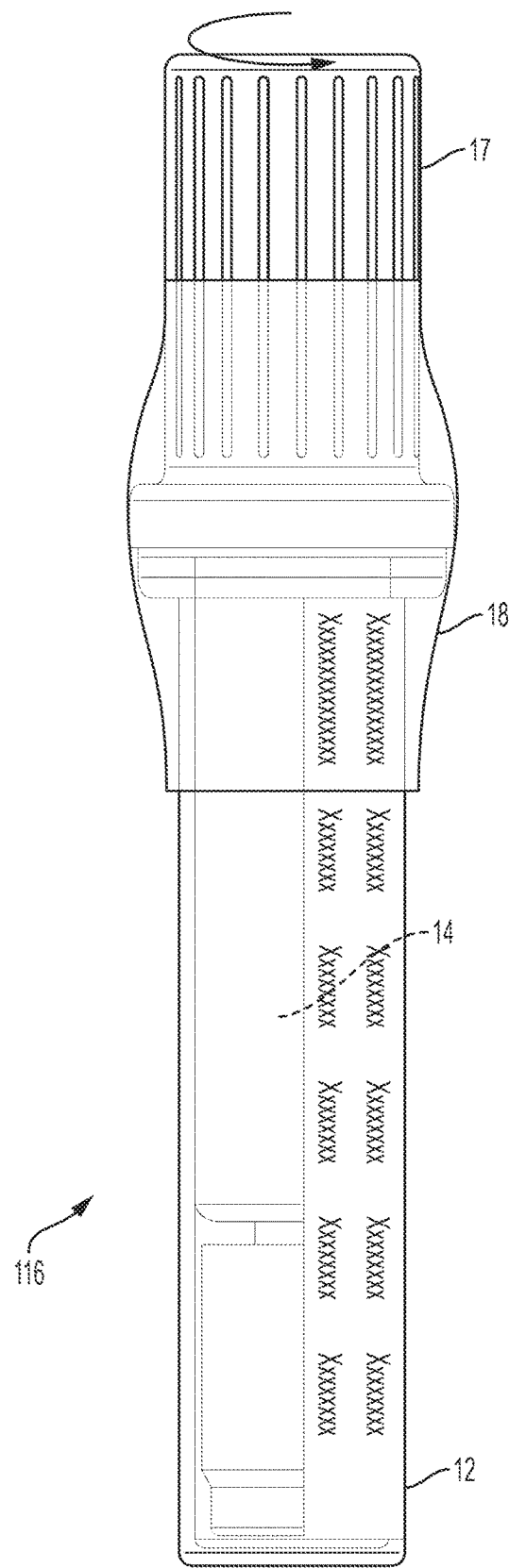
FIG. 27 is an elevation view of a viewing window of a syringe packaging system in accordance with an embodiment of the present invention.
Figure 28:
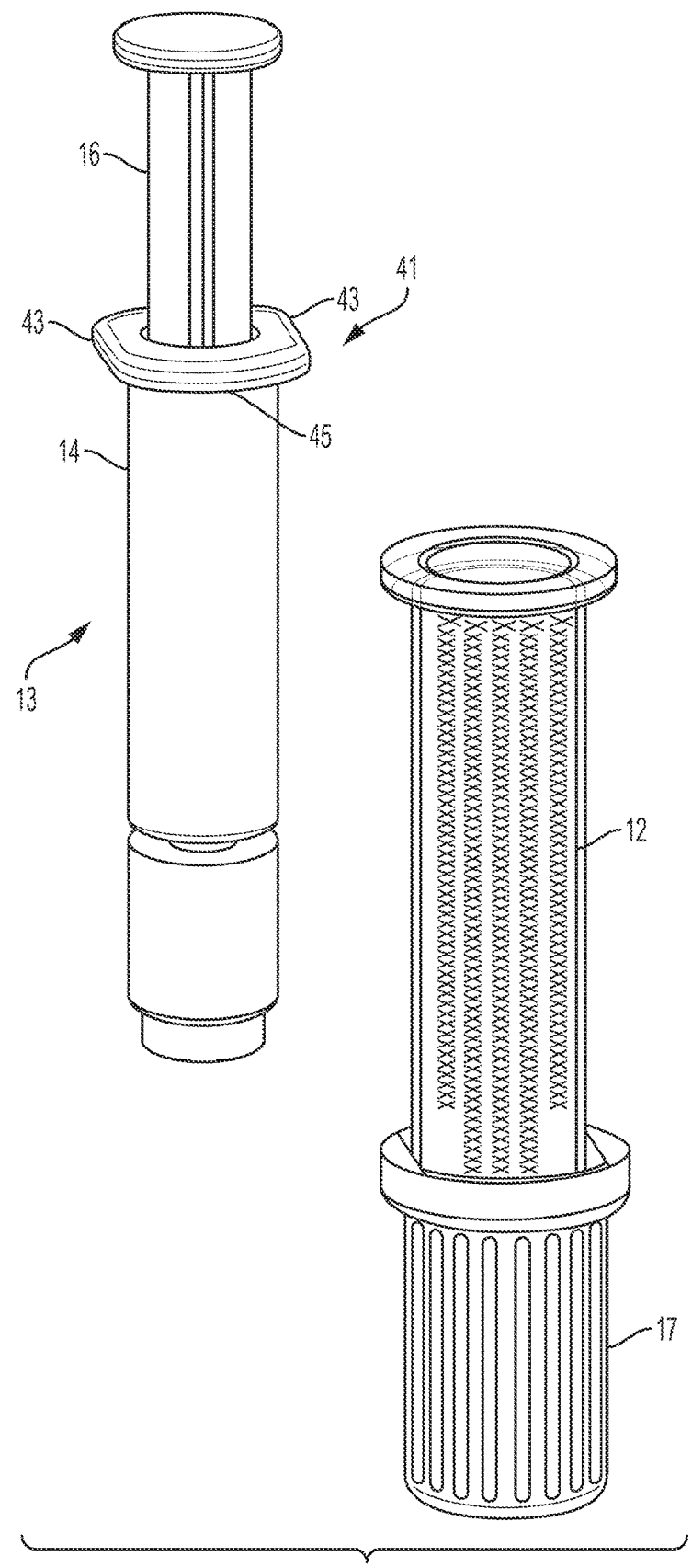
FIG. 28 is an exploded, perspective view of a syringe packaging system in accordance with an embodiment of the present invention.
Figure 29:
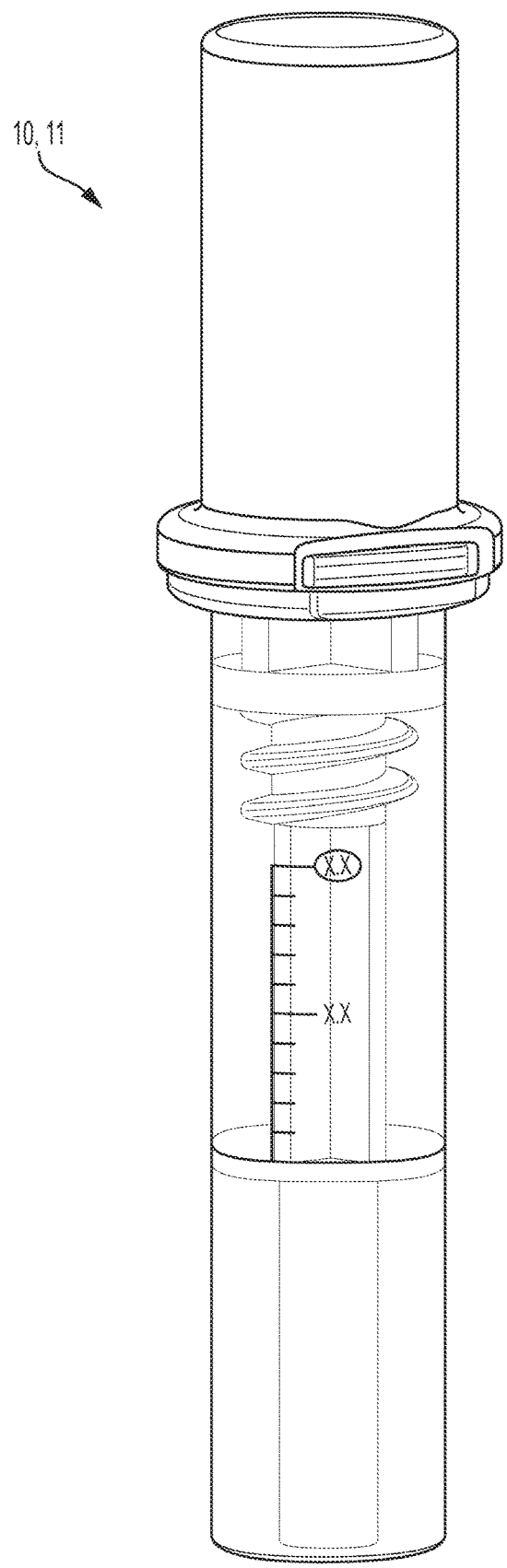
FIG. 29 is a perspective view of a syringe packaging system in accordance with an embodiment of the present invention.
Figure 30:
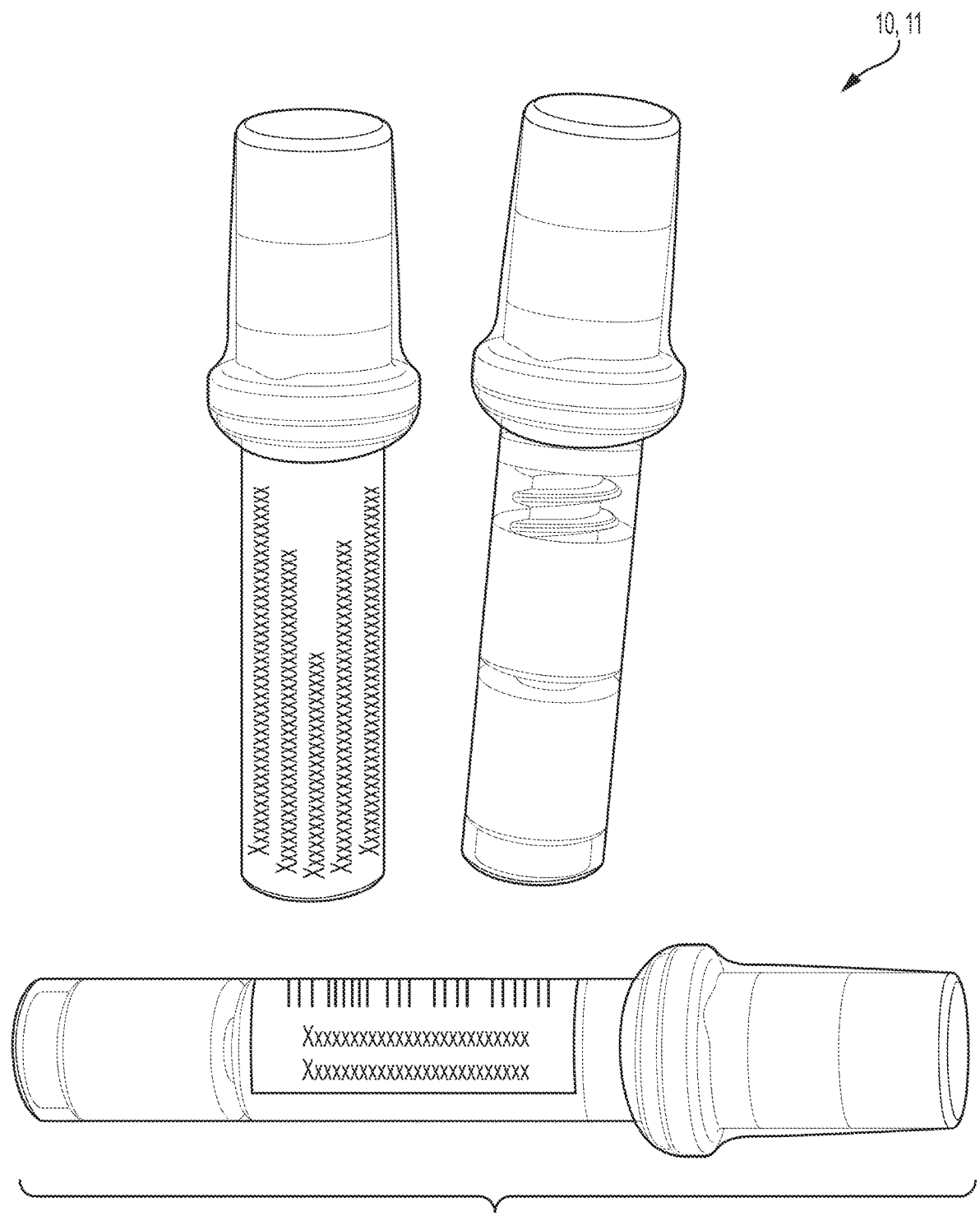
FIG. 30 is a perspective view of a plurality of syringe packaging systems in accordance with an embodiment of the present invention.

Referring to FIGS. 1-39, syringe barrel 14 generally includes a barrel body having a sidewall 30 extending between a first or distal end 32 and a second or proximal end 34. Sidewall 30 defines an elongate aperture or interior chamber 36 of syringe barrel 14. In one embodiment, interior chamber 36 may span the extent of syringe barrel 14 so that syringe barrel 14 is cannulated along its entire length. In one embodiment, syringe barrel 14 may be in the general form of an elongated cylindrical barrel as is known in the art in the general shape of a hypodermic syringe. In alternative embodiments, syringe barrel 14 may be in other forms for containing a fluid for delivery, such as in the general form of an elongated rectangular barrel, for example. Syringe barrel 14 may be formed of glass, or may be injection molded from thermoplastic material such as polypropylene and polyethylene according to techniques known to those of ordinary skill in the art, though it is to be appreciated that syringe barrel 14 may be made from other suitable materials and according to other applicable techniques. In certain configurations, syringe barrel 14 may include an outwardly extending flange 40 about at least a portion of proximal end 34. Flange 40 may be configured for easy grasping by a medical practitioner, as will be discussed herein. In one embodiment, flange 40 is a cut flange 41. Referring to FIG. 17, in one embodiment, the cut flange 41 includes a first flat wall portion 43 and a first arcuate wall portion 45.

Distal end 32 of syringe barrel 14 includes an outlet opening 38 (FIGS. 15 and 16) which is in fluid communication with chamber 36. Outlet opening 38 may be sized and adapted for engagement with a separate device, such as a needle assembly or IV connection assembly and, therefore, may include a mechanism for such engagement as is conventionally known. For example, distal end 32 may include a generally-tapered luer tip for engagement with an optional separate tapered luer structure of such a separate device for attachment therewith (not shown). In one configuration, both the tapered luer tip and the separate tapered luer structure may be provided with the syringe assembly 13. In such a configuration, the separate tapered luer structure may be fitted with an attachment mechanism, such as a threaded engagement, for corresponding engagement with a separate device (not shown). In another configuration, the tapered luer tip may be provided for direct engagement with a separate device (not shown). In addition, a mechanism for locking engagement therebetween may also be provided with at least one of the tapered luer tip and/or the separate tapered luer structure, such as a luer collar or luer lock including interior threads. Such luer connections and luer locking mechanisms are well known in the art.

Proximal end 34 of syringe barrel 14 is generally open-ended, but is intended to be closed off to the external environment as discussed herein. Syringe barrel 14 may also include markings, such as graduations located on sidewall 30, for providing an indication as to the level or amount of fluid contained within interior chamber 36 of syringe barrel 14. Such markings may be provided on an external surface of sidewall 30, an internal surface of sidewall 30, or integrally formed or otherwise within sidewall 30 of syringe barrel 14. In other embodiments, alternatively, or in addition thereto, the markings may also provide a description of the contents of the syringe or other identifying information as may be known in the art, such as maximum and/or minimum fill lines.

Syringe barrel 14 may be useful as a pre-filled syringe, and, therefore, may be provided for end use with a fluid F (FIG. 16), such as a medication or drug, contained within interior chamber 36 of syringe barrel 14, pre-filled by the manufacturer. In this manner, syringe barrel 14 can be manufactured, pre-filled with a medication, sterilized, and packaged in appropriate packaging such as tube 12 and cap 17 for delivery, storage, and use by the end user, without the need for the end user to fill the syringe with medication from a separate vial prior to use. In one embodiment, syringe barrel 14 may include a tip cap or sealing cap member 42 including a seal 44 disposed at distal end 32 of syringe barrel 14 to seal a fluid F, such as a medication, within interior chamber 36 of syringe barrel 14. In one embodiment, seal 44 may be formed of a pierceable elastomer material.

As used herein, the term "drug" and/or "medication" refers to a pharmaceutically active ingredient(s) and any pharmaceutical liquid composition containing the pharmaceutically active ingredient(s). Pharmaceutical liquid compositions include forms such as solutions, suspensions, emulsions, and the like. These pharmaceutical liquid compositions can be administered orally or by injection.

Referring to FIGS. 15 and 16, syringe assembly 13 includes stopper 19 which is moveably or slidably disposed within interior chamber 36 of syringe barrel 14, and in sealing contact with the internal surface of sidewall 30 of syringe barrel 14. Stopper 19 is sized relative to syringe barrel 14 to provide sealing engagement with the interior surface of sidewall 30 of syringe barrel 14. Additionally, stopper 19 may include one or more annular ribs extending around the periphery of stopper 19 to increase the sealing engagement between stopper 19 and the interior surface of sidewall 30 of syringe barrel 14. In alternate embodiments, a singular O-ring or a plurality of O-rings may be circumferentially disposed about stopper 19 to increase the sealing engagement with the interior surface of sidewall 30 of syringe barrel 14.

Figure 13:
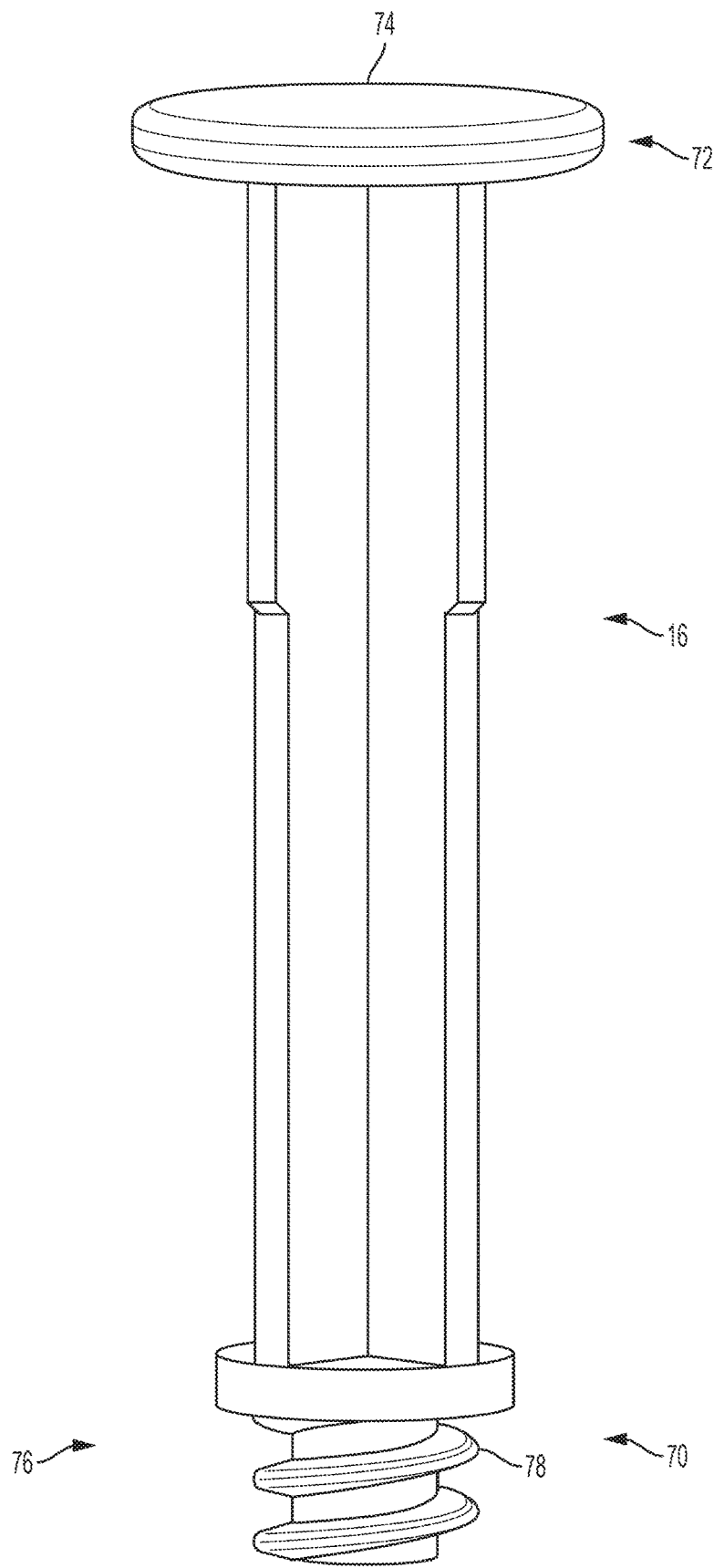
FIG. 13 is a perspective view of a plunger rod in accordance with an embodiment of the present invention.
Figure 14:
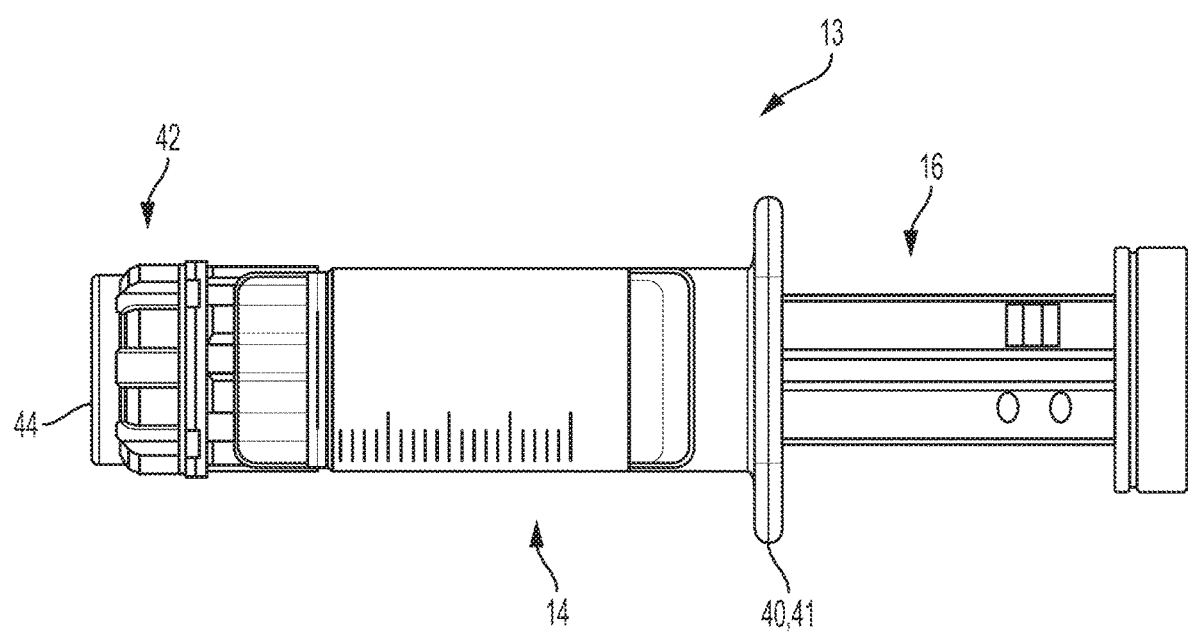
FIG. 14 is an elevation view of a syringe in accordance with an embodiment of the present invention.

Referring to FIG. 13, in one embodiment, stopper 19 includes a first or distal end 50 and a second or proximal end 52 defining a plunger receiving aperture 54 formed therein and having a securement feature or engagement portion 56 for securing plunger rod 16 to stopper 19. In one embodiment, referring to FIG. 13, the engagement portion 56 may include a threaded portion 58.

Referring to FIG. 13, syringe assembly 13 further includes plunger rod 16 which provides a mechanism for dispensing fluid contained within interior chamber 36 of syringe barrel 14 through outlet opening 38 upon connection of plunger rod 16 to syringe barrel 14 via stopper 19 as will be described in more detail below. Plunger rod 16 is adapted for advancing stopper 19. For example, the plunger rod 16 is able to advance stopper 19 between the positions shown in FIGS. 15 and 16. In one embodiment, plunger rod 16 is sized for movement within interior chamber 36 of syringe barrel 14, and generally includes a first or distal end 70, a second or proximal end 72, a flange 74 disposed adjacent second end 72, and a securement feature or engagement portion 76 for securing plunger rod 16 to stopper 19. In one embodiment, referring to FIGS. 15 and 16, the engagement portion 76 of plunger rod 16 may include a threaded portion 78. In one embodiment, the flange 74 forms a thumb pad for a user to manipulate the plunger rod 16. In one embodiment, the engagement portion 76 is disposed adjacent the first end 70.

In one embodiment, plunger rod 16 can be secured to stopper 19 by threadingly engaging threaded portion 58 of stopper 19 to threaded portion 78 of plunger rod 16 as shown in FIGS. 15 and 16. In other embodiments, plunger rod 16 can be secured to stopper 19 using a snap fit mechanism, a ball detent, locking tabs, spring loaded locking mechanism, latch, adhesive, or other similar mechanism. In all embodiments, plunger rod 16 is locked, secured, or engaged to stopper 19, i.e., significant relative movement between plunger rod 16 and stopper 19 is prevented.

In some embodiments, plunger rod 16 and stopper 19 may be co-formed such as by co-extrusion. In other embodiments, plunger rod 16 and stopper 19 may be integrally formed as a plunger/stopper assembly.

Figures 11, 12:
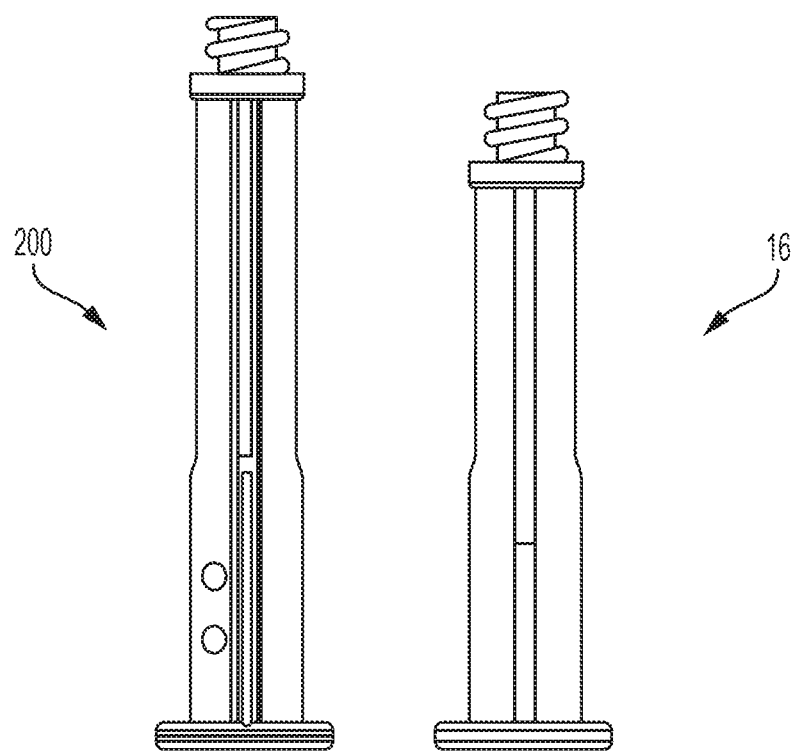
FIG. 11 is a front view of a standard plunger rod.
FIG. 12 is a front view of a plunger rod in accordance with an embodiment of the present invention.

Referring to FIGS. 11 and 12, in one embodiment, the length of a plunger rod 16 of the present disclosure (FIG. 12) is shorter than the length of a conventional or standard plunger rod 200 (FIG. 11). In this manner, a plunger rod 16 of the present disclosure allows for reduced storage space of a pre-filled syringe.

Additionally, at the end of the injection, when the entire drug has been delivered, the thumb pad or flange 74 of the plunger rod 16 of the present disclosure is much closer to the flange 40 of the syringe barrel 14 than a standard syringe is. For example, in one embodiment, the distance between an upper surface of the flange 40 of the syringe barrel 14 and a lower surface of the flange 74 of the plunger rod 16 may be between 0.5 to 2.5 mm. In another embodiment, the distance between an upper surface of the flange 40 of the syringe barrel 14 and a lower surface of the flange 74 of the plunger rod 16 may be between 0.9 to 2.3 mm. In another embodiment, the distance between an upper surface of the flange 40 of the syringe barrel 14 and a lower surface of the flange 74 of the plunger rod 16 may be around 1.6 mm. In this manner, the global length of a prefilled syringe is reduced, leading to a smaller required space for storage.

Figure 5:
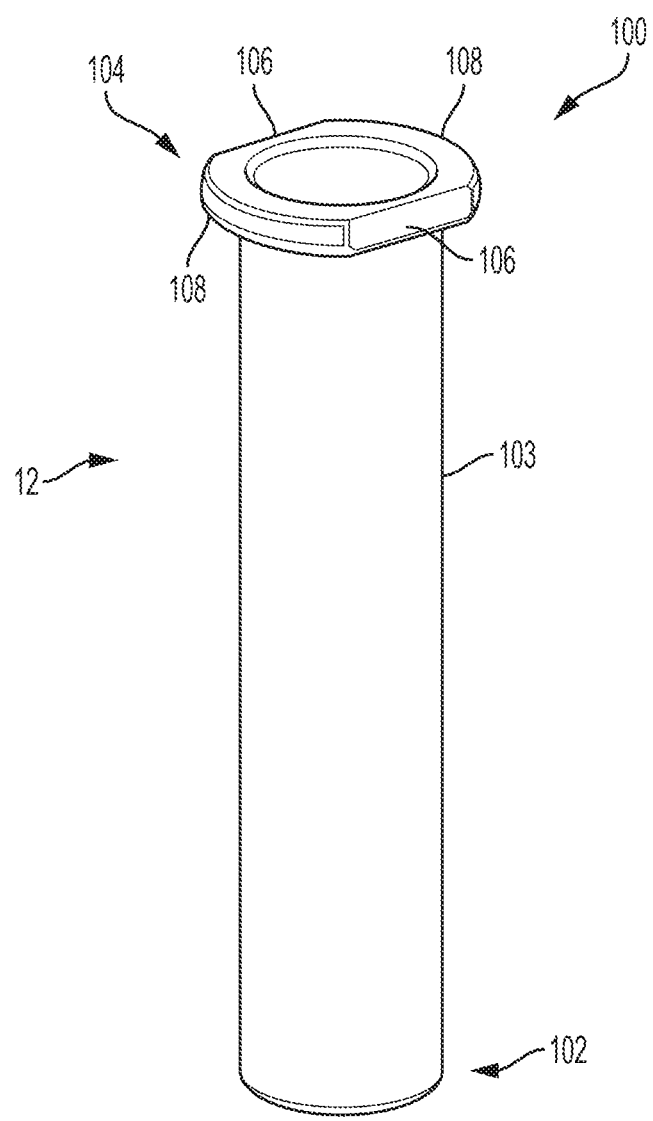
FIG. 5 is a perspective view of a tube in accordance with an embodiment of the present invention.
Figure 6:
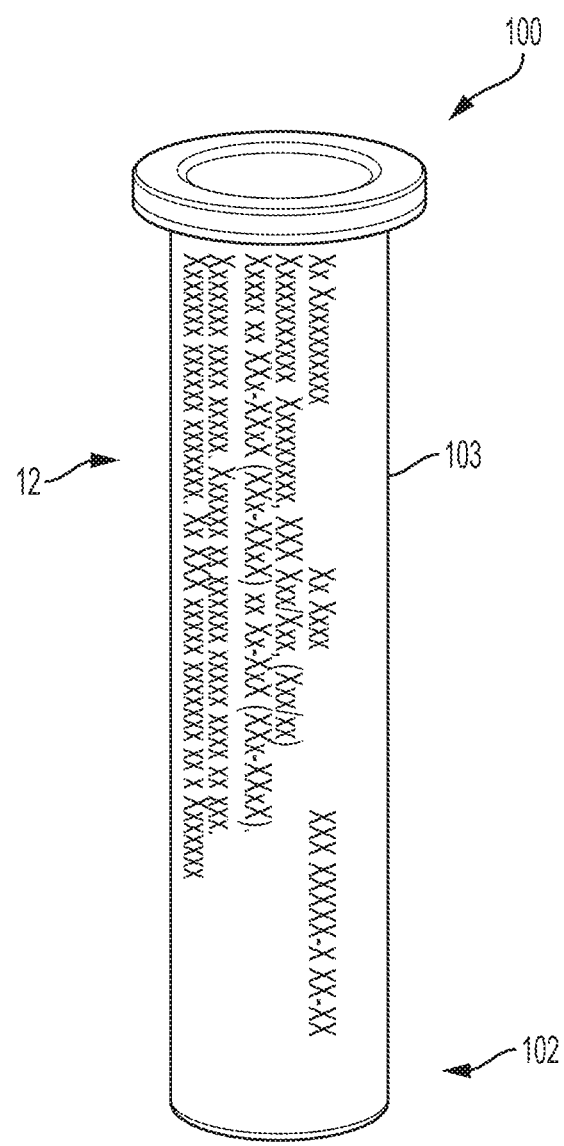
FIG. 6 is a perspective view of a tube with a label in accordance with an embodiment of the present invention.
Figure 7:
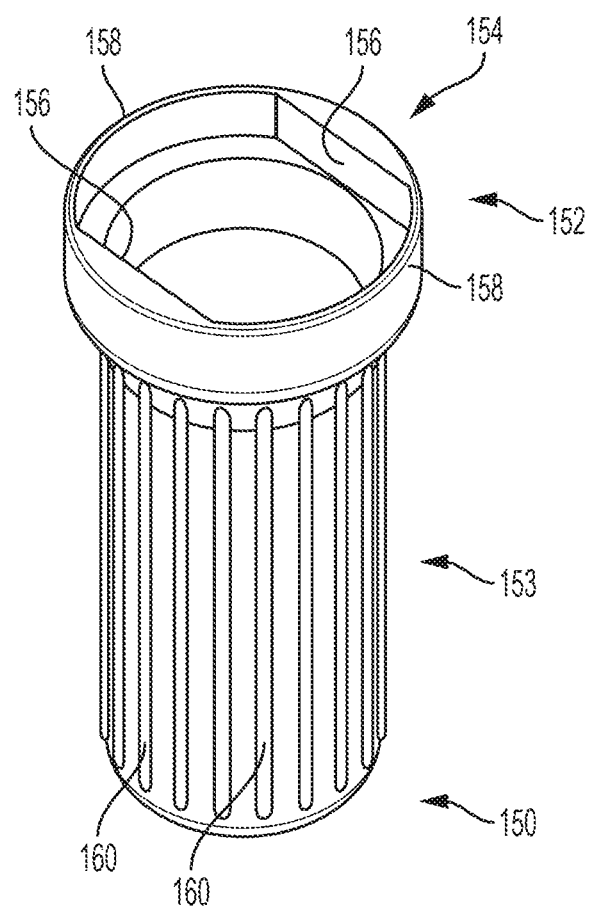
FIG. 7 is a perspective view of a cap in accordance with an embodiment of the present invention.
Figure 8:
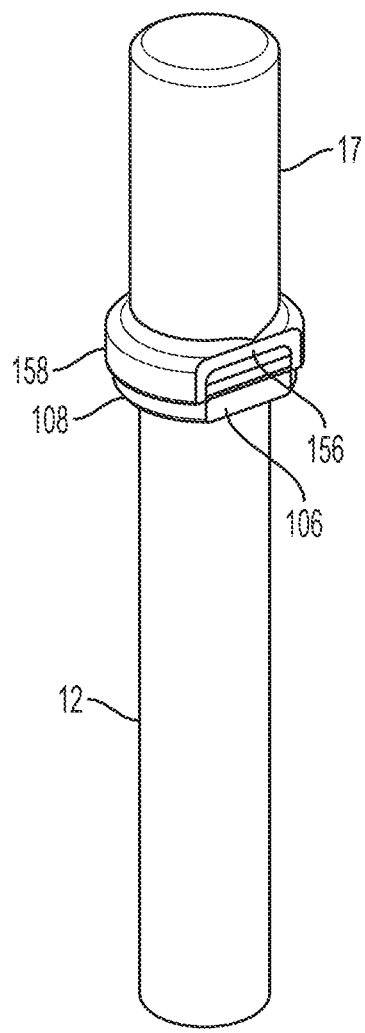
FIG. 8 is a perspective view of a packaging member in accordance with an embodiment of the present invention.
Figure 9:
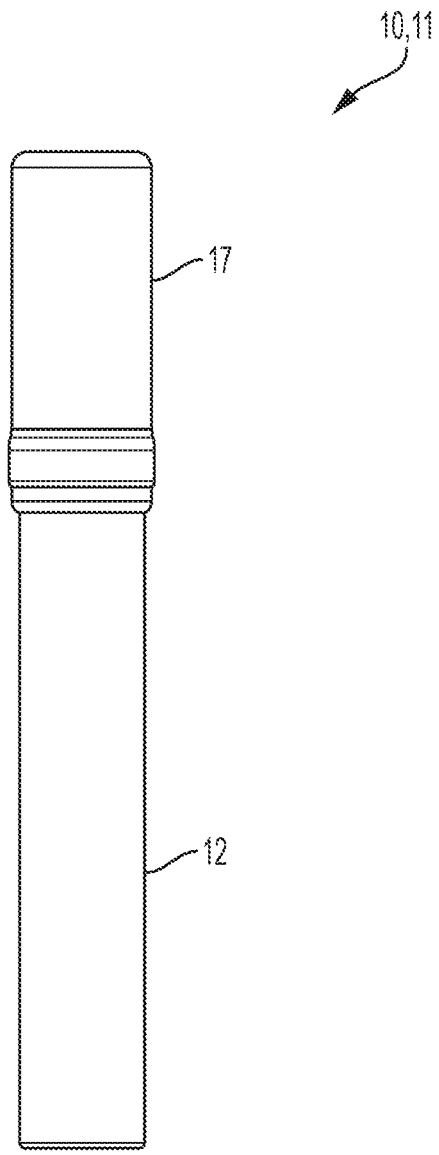
FIG. 9 is an elevation view of a packaging member in accordance with an embodiment of the present invention.
Figure 10:
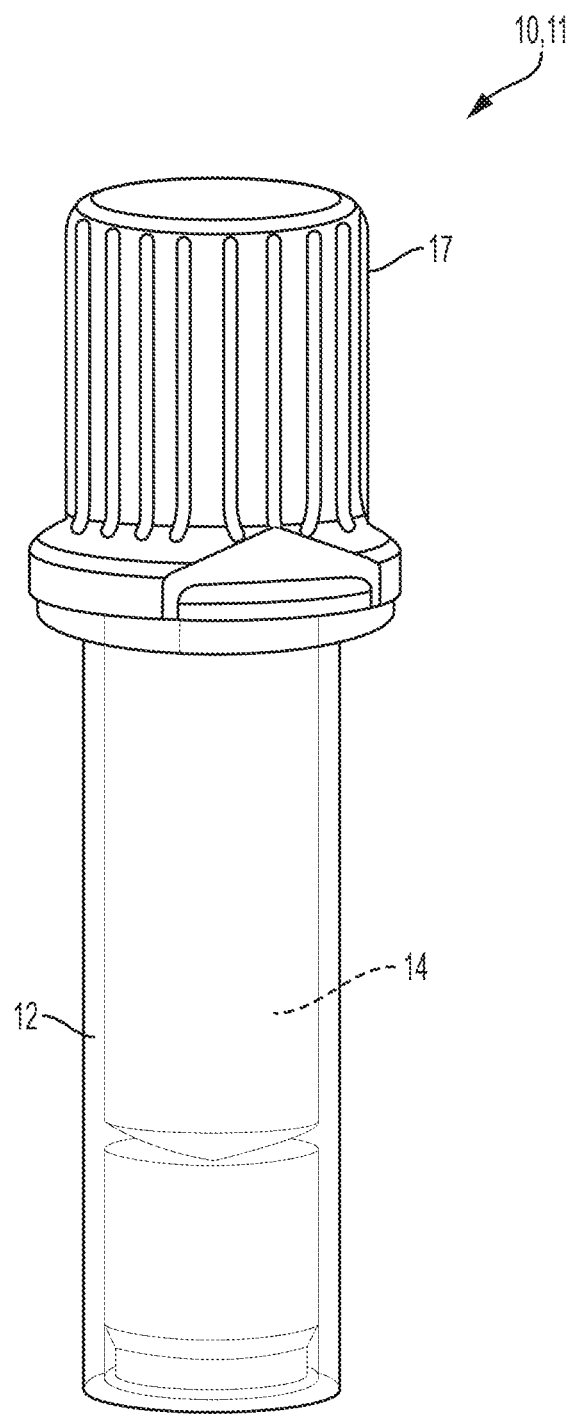
FIG. 10 is a perspective view of a packaging member in accordance with another embodiment of the present invention.

Referring to FIG. 5, a tube 12 of the present disclosure encloses the syringe barrel 14 and includes a proximal end 100, a distal end 102, and a sidewall 103 extending therebetween. In one embodiment, the proximal end 100 of the tube 12 includes a tube cut flange 104. In one embodiment, the tube cut flange 104 includes a second flat wall portion 106 and a second arcuate wall portion 108. The distal end 102 of the tube 12 is closed. The tube 12 of the present invention provides a mechanical protection of the syringe barrel 14 that is contained inside. The tube 12 also provides a good support for labeling.

Referring to FIGS. 1-3, 8, and 9, with the syringe barrel 14 contained within the tube 12, the cut flange 41 of the syringe barrel 14 is aligned with the tube cut flange 104. For example, the first flat wall portion 43 of the cut flange 41 of the syringe barrel 14 is aligned with the second flat wall portion 106 of the tube 12 and the first arcuate wall portion 45 of the cut flange 41 of the syringe barrel 14 is aligned with the second arcuate wall portion 108 of the tube 12. The alignment of the cut flange 41 of the syringe barrel 14 with the tube cut flange 104 of the tube 12 minimizes the global size of the packaging of the present disclosure.

The tube 12 of the present disclosure provides mechanical protection of the syringe barrel 14 and the flange 40, 41 of the syringe barrel 14 with the flange 40, 41 of the syringe barrel 14 being supported by the tube cut flange 104 of the tube 12.

In one embodiment, the tube 12 may be formed of a plastic material. For example, the tube 12 may be formed of polyethylene terephthalate (PET), polypropylene (PP), polycarbonate (PC), or other material. In one embodiment, the tube 12 is formed of a transparent material. In this manner, referring to FIG. 27, a portion of the tube 12 forms a viewing window 116 that allows a user to see data and/or information written on an outer surface of the syringe barrel 14. Thus, the tube 12 of the present disclosure provides access to the essential data/information that is written on a surface of the syringe barrel 14 placed inside the tube 12, as well as the tube 12 provides visual access to the contents of the syringe barrel 14.

The closed distal end 102 of the tube 12 acts as a barrier to avoid any piercing and/or withdrawal of a drug contained inside the syringe 13 through a seal 44 of the pre-filled syringe 13, with a needle, for example. In this manner, with the syringe barrel 14 enclosed within the tube 12, the closed distal end 102 of the tube 12 shields the distal end 32 and the seal 44 of the syringe barrel 14. The tube 12 prevents any piercing of the syringe barrel 14 and avoids any withdrawal of a drug contained inside the syringe barrel 14.

In one embodiment, the thickness of the flange 104 of the tube 12 is between 1 mm and 3 mm. In this manner, the thickness of the flange 104 of the tube 12 prevents the tube 12 from passing under or being removed from the film 18 in the final packaging. For example, if someone tries to pull on the tube 12 in a distal direction to slide the tube 12 under the film 18.

Referring to FIGS. 1-10 and 17-19, a cap 17 of the present disclosure, along with the tube 12, encloses the syringe 13. In one embodiment, the cap 17 includes a first end 150, a second end 152, and a sidewall 153 extending therebetween. The second end 152 includes a cut skirt 154.

In one embodiment, the cut skirt 154 includes a third flat wall portion 156 and a third arcuate wall portion 158. With the pre-filled syringe 13 enclosed within the packaging member 11, the cut skirt 154 of the cap 17 surrounds the cut flange 41 of the syringe barrel 14. The tube 12 and the cap 17 of the present disclosure provides mechanical protection of the syringe 13 and the flange 40, 41 of the syringe barrel 14 with the flange 40, 41 of the syringe barrel 14 being supported by the tube cut flange 104 of the tube 12 and surrounded by the cut skirt 154 of the cap 17.

The cut skirt 154 of the cap 17 provides mechanical protection of the plunger rod 16 and of the flange 40, 41 of the syringe barrel 14. The cut skirt 154 of the cap 17 also prevents any access to the stopper 19 and/or other areas of the syringe 13, thereby preventing any potential of undesired drug withdrawal from the syringe 13.

In one embodiment, as described above, the cut skirt 154 of the cap 17 surrounds the flange 104 of the tube 12. In such embodiments, the flange 40, 41 of the syringe barrel 14 is not visible and is also not accessible.

Referring to FIG. 17, in one embodiment, the skirt 154 is cut to have the same shape as the flange 104 of the tube 12. The tube 12 is able to perfectly fit with the cap 17 and the cut parts are aligned and the global size is optimized. For example, the cut skirt 154 of the cap 17 is aligned with the cut flange 104 of the tube 12. The alignment of the cut skirt 154 of the cap 17 with the tube cut flange 104 of the tube 12 minimizes the global size of the packaging of the present disclosure. Furthermore, the cut skirt 154 of the cap 17 protects the flange 40, 41 of the syringe barrel 14 which is not accessible.

In one embodiment, the surface of the cap 17 is an ideal area to stick an adhesive label with the information required for such a device and the drugs contained inside the syringe 13.

In one embodiment, the cap 17 has an easy grip surface with longitudinal ribs 160. In other embodiments, the cap 17 can have other surfaces, for example, a flat surface.

In one embodiment, the cap 17 may be formed of a plastic material. For example, the cap 17 may be formed of an opaque material, polyethylene terephthalate (PET), polypropylene (PP), polycarbonate (PC), or other material.

Referring to FIGS. 1-4 and 17-19, the packaging member 11 includes a film 18 that is securable to a portion of the tube 12 and a portion of the cap 17 to connect the tube 12 and the cap 17 with the pre-filled syringe 13 enclosed within the cap 17 and the tube 12. In this manner, the film 18, together with the tube 12 and the cap 17, provides protection of the syringe 13, reduces the global size of the packaging, and allows for easy storage in a storage unit.

In one embodiment, the film 18 comprises a shrinkable film. The film 18 can include a tamper evident sleeve.

The film 18 of the present disclosure is used as a tamper evidence feature. Additionally, the film 18 of the present disclosure maintains together and connects the tube 12 and the cap 17. Furthermore, the film 18 of the present disclosure also provides proof of the package integrity maintenance.

In one embodiment, the film 18 includes circular pre-cut perforations 28 to facilitate the opening of the film 18 and the removal of the syringe 13 from the packaging assembly 11.

In some embodiments, the tamper evidence features may include breaking tabs that connect a ring to the skirt 154 of the cap 17. In such embodiments, the ring can be positioned under the flange 104 of the tube 12 and remain at this position after the breakage of the tabs leading to the opening of the packaging.

All of the components of syringe packaging system 10 may be constructed of any known material, and are desirably constructed of medical-grade polymers.

Referring to FIGS. 1-39, packaging of a syringe 13 within packaging assembly 11 will now be described. Initially, syringe barrel 14, plunger rod 16, tube 12, and cap 17 are sterilized according to techniques known to those of ordinary skill in the art. In some embodiments, syringe barrel 14 may be pre-filled as described above.

Next, a plunger rod 16 of the present disclosure can be connected to the syringe 13 via engagement of the securement feature 76 of the plunger rod 16 with the engagement portion 56 of the stopper 19 as shown in FIGS. 15 and 16. Referring to FIGS. 1-3 and 17, the syringe 13 can be loaded within the tube 12 such that the closed distal end 102 of the tube 12 shields the distal end 32 of the syringe barrel 14. The tube 12 of the present disclosure provides mechanical protection of the syringe barrel 14 and the flange 40, 41 of the syringe barrel 14 with the flange 40, 41 of the syringe barrel 14 being supported by the tube cut flange 104 of the tube 12.

Next, the cap 17 is positioned over the plunger rod 16 and in engagement with the tube 12 as described above. For example, with the pre-filled syringe 13 enclosed within the packaging member 11, the cut skirt 154 of the cap 17 surrounds the cut flange 41 of the syringe barrel 14. The tube 12 and the cap 17 of the present disclosure provides mechanical protection of the syringe 13 and the flange 40, 41 of the syringe barrel 14 with the flange 40, 41 of the syringe barrel 14 being supported by the tube cut flange 104 of the tube 12 and surrounded by the cut skirt 154 of the cap 17.

Figure 2:
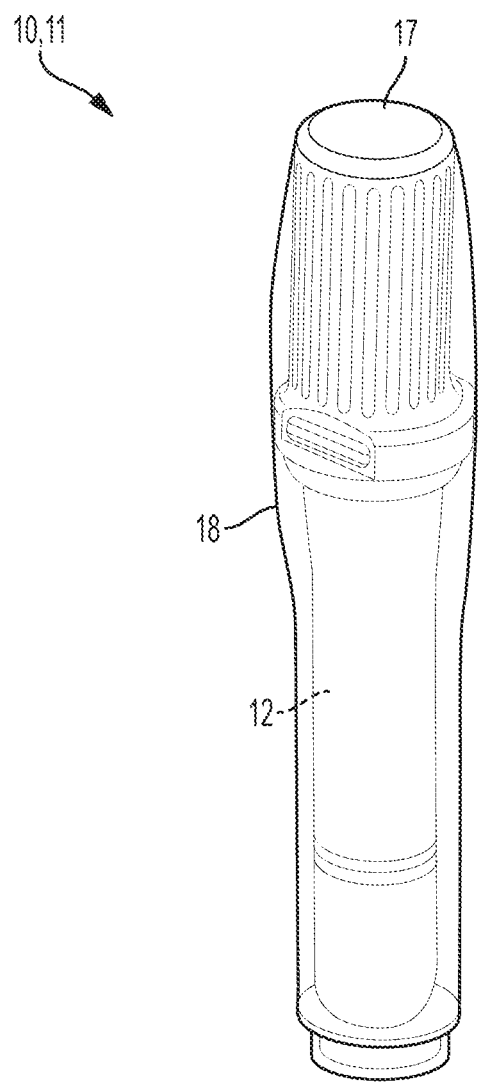
FIG. 2 is a perspective view of a syringe packaging system in accordance with another embodiment of the present invention.
Figure 3:
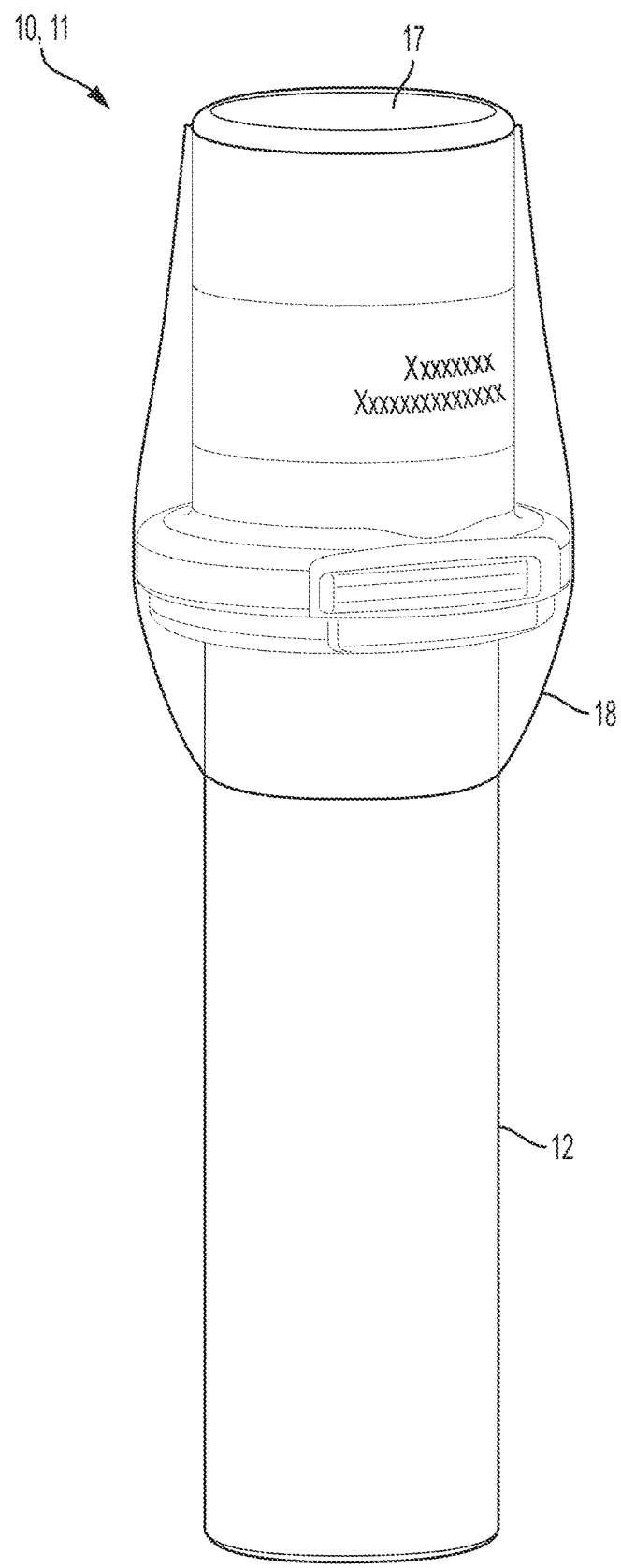
FIG. 3 is a perspective view of a syringe packaging system in accordance with another embodiment of the present invention.
Figure 4:
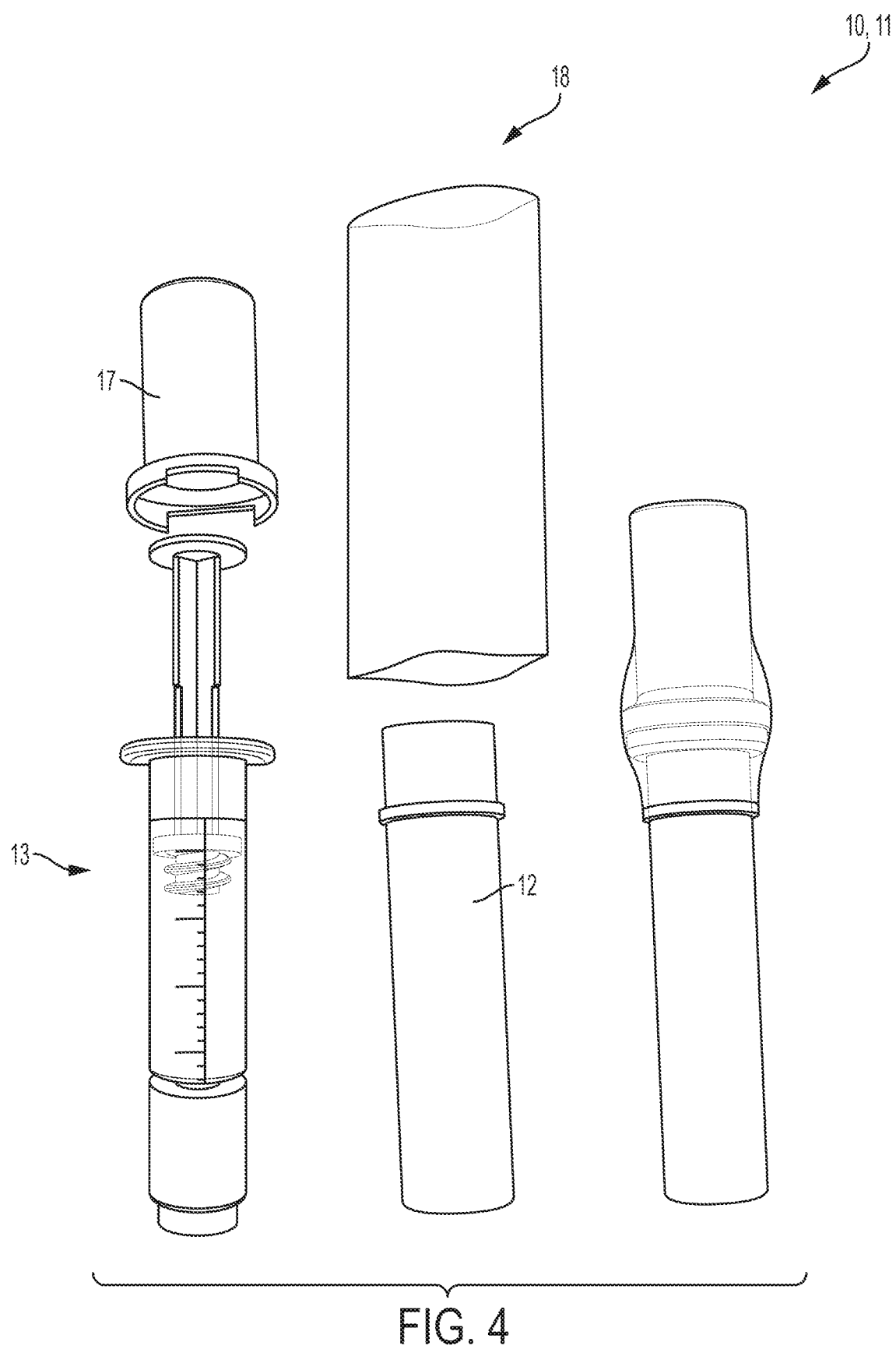
FIG. 4 is an exploded, perspective view of a syringe packaging system in accordance with an embodiment of the present invention.
Figure 31:
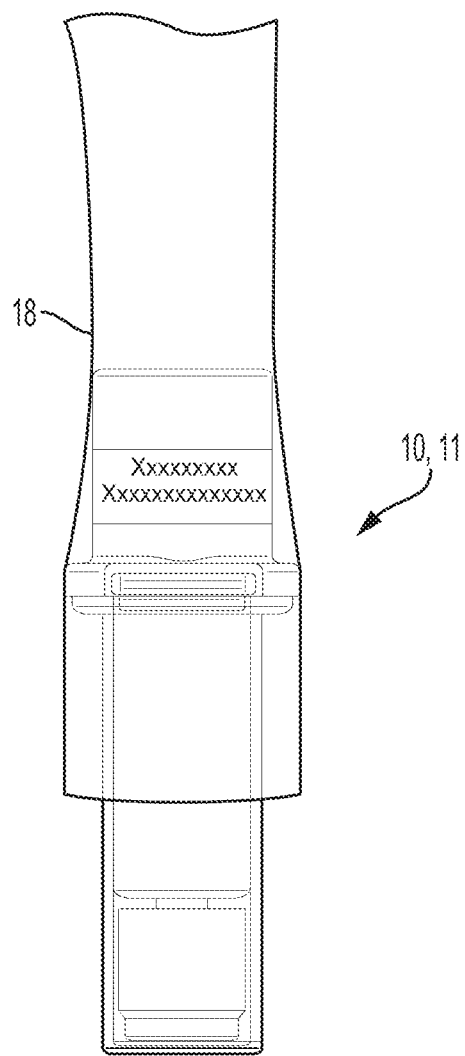
FIG. 31 is a perspective view of a syringe packaging system in accordance with another embodiment of the present invention.

Next, the film 18 is secured to a portion of the tube 12 and a portion of the cap 17 to connect the tube 12 and the cap 17 with the pre-filled syringe 13 enclosed within the cap 17 and the tube 12. Referring to FIGS. 1 and 3, in some embodiments, the film 18 covers a portion of the tube 12 and a portion of the cap 17. Referring to FIGS. 2 and 31, in other embodiments, the film 18 is able to cover a larger portion of the tube 12 and/or a larger portion of the cap 17.

Referring to FIGS. 32-39, a process of removing a syringe 13 from the packaging assembly 11 of the present disclosure will now be described.

Figure 32:
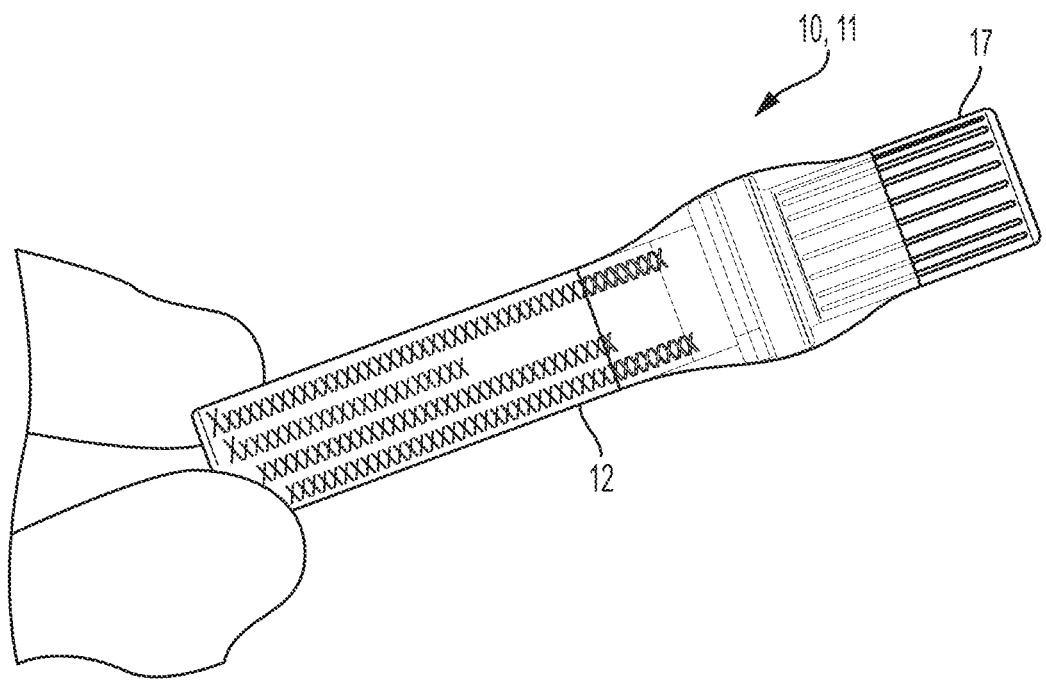
FIG. 32 is a perspective view of a first step of using a device of the present disclosure in accordance with an embodiment of the present invention.

Referring to FIG. 32, when a user desires to remove the syringe 13 from the packaging assembly 11, a user may inspect the packaging assembly 11 by verifying: (1) the tube and cap integrity; (2) the tamper evident sleeve integrity; and (3) if the tamper evident sleeve has been damaged, the syringe 13 is not used.

Figure 33:
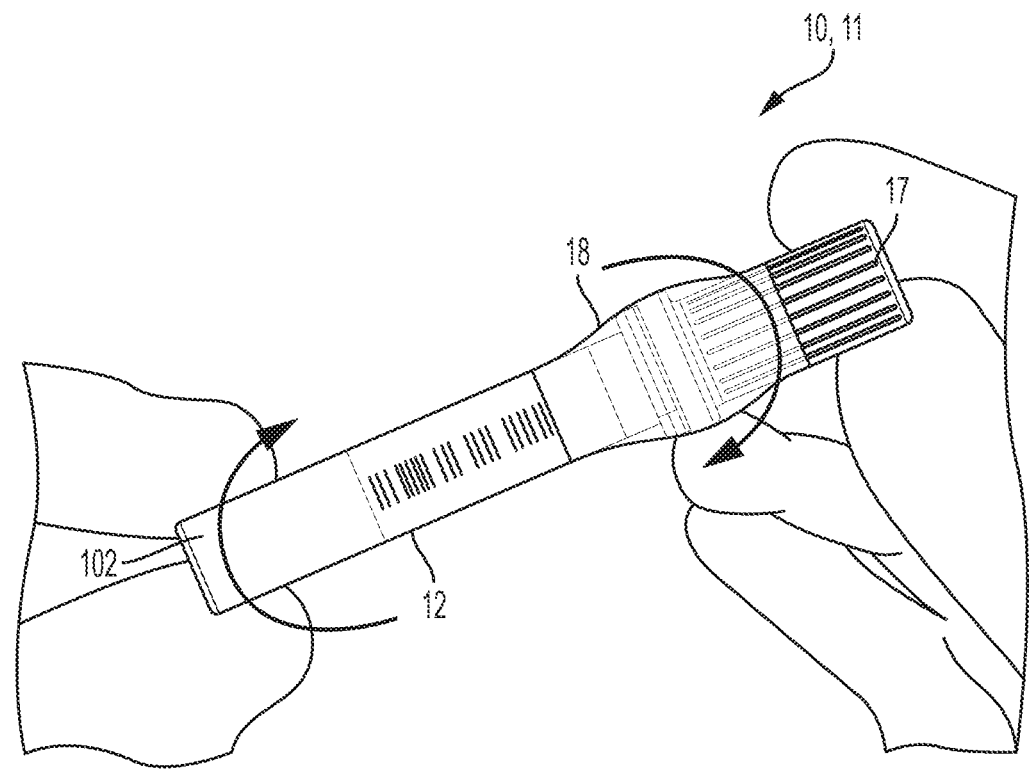
FIG. 33 is a perspective view of a second step of using a device of the present disclosure in accordance with an embodiment of the present invention.
Figure 34:
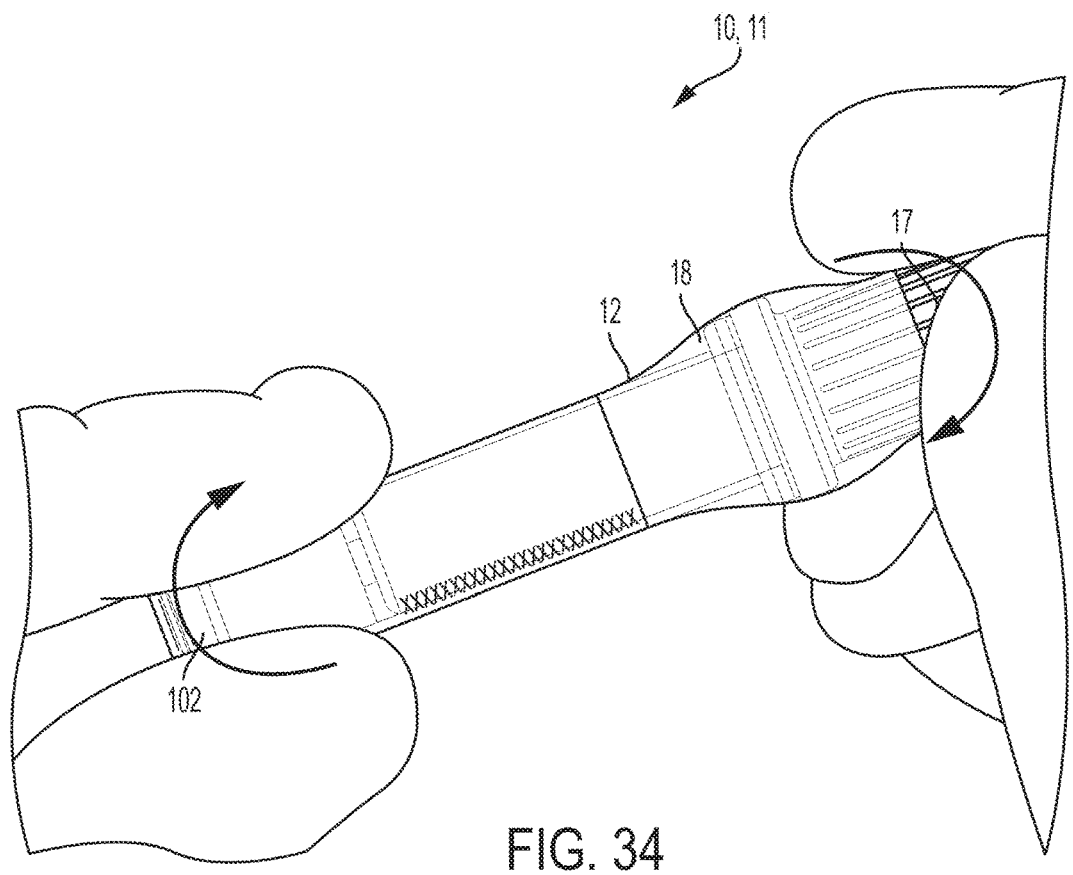
FIG. 34 is a perspective view of a third step of using a device of the present disclosure in accordance with an embodiment of the present invention.

Referring to FIGS. 33 and 34, to visualize a bar code and/or any other relevant information and inspect the contents of the syringe prior to opening, the lower end 102 of the tube 12 may be held and the cap 17 rotated relative to the tube 12 to visualize. For example, referring to FIG. 27, a portion of the tube 12 forms a viewing window 116 that allows a user to see data and/or information written on an outer surface of the syringe barrel 14. Thus, the tube 12 of the present disclosure provides access to the essential data/information that is written on a surface of the syringe barrel 14 placed inside the tube 12, as well as the tube 12 provides visual access to the contents of the syringe barrel 14.

Figure 35:
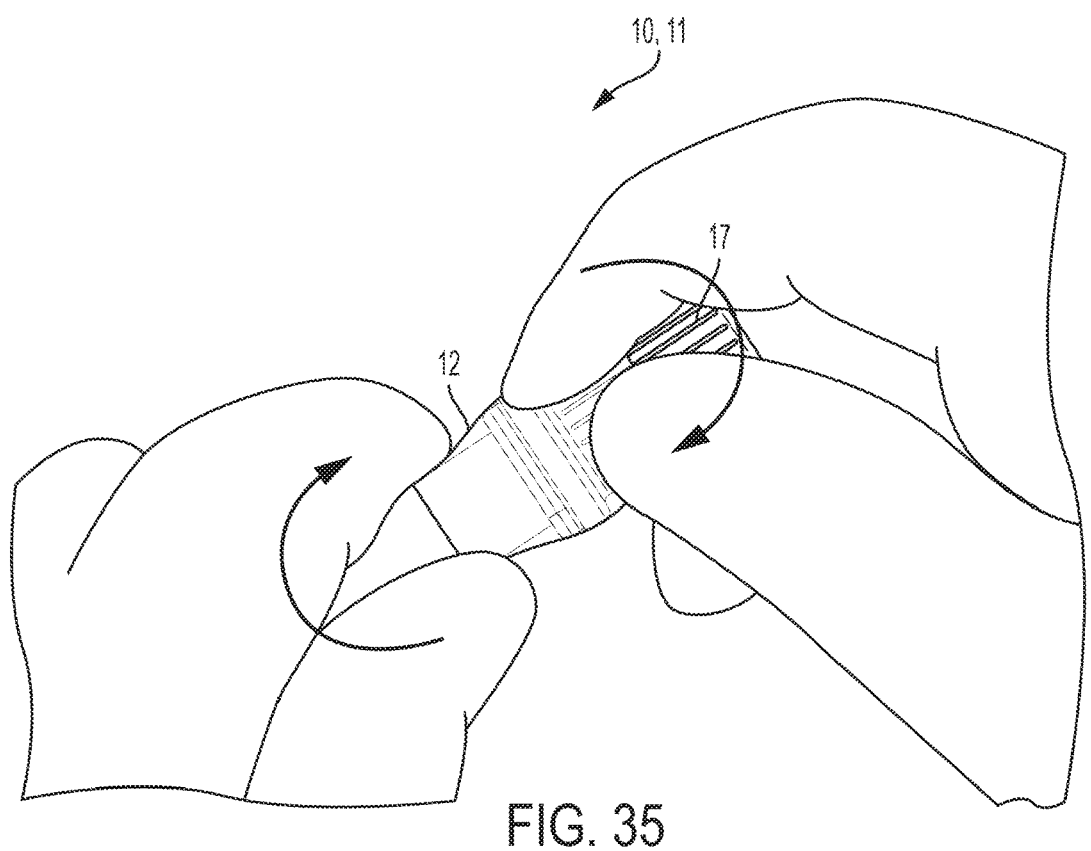
FIG. 35 is a perspective view of a fourth step of using a device of the present disclosure in accordance with an embodiment of the present invention.

Referring to FIG. 35, to open the packaging assembly 11, the cap 17 and the tube 12 are held, grasping the tamper evident sleeve, on either side of the syringe flange. Next, the film 18 can be twisted until the tamper evident sleeve breaks and the cap 17 and the tube 12 separate.

Figure 36:
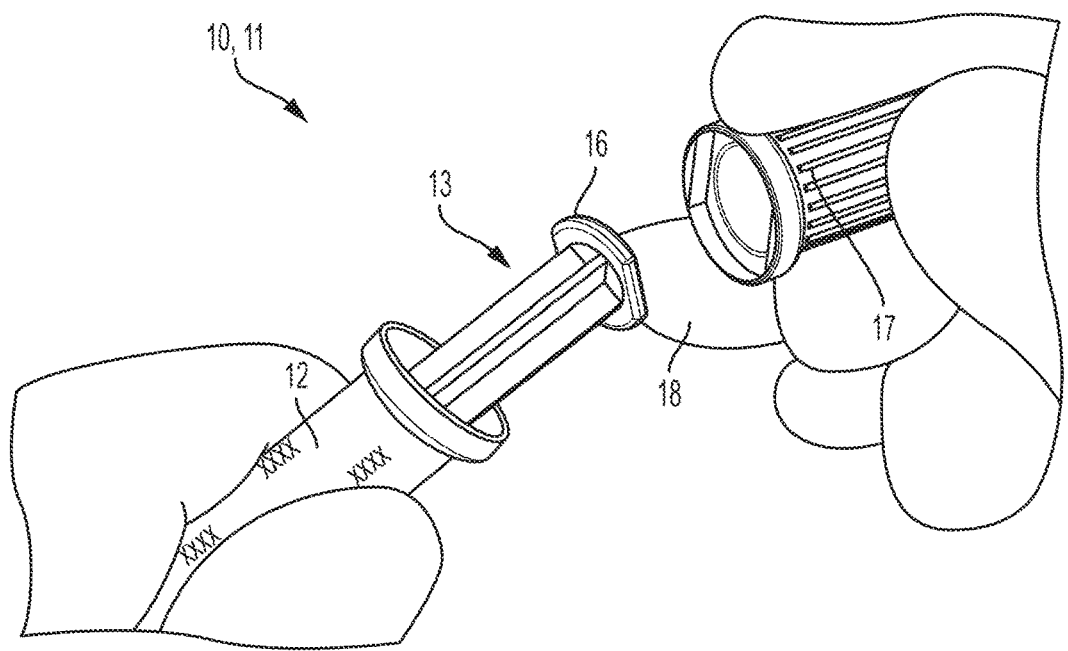
FIG. 36 is a perspective view of a fifth step of using a device of the present disclosure in accordance with an embodiment of the present invention.
Figure 37:
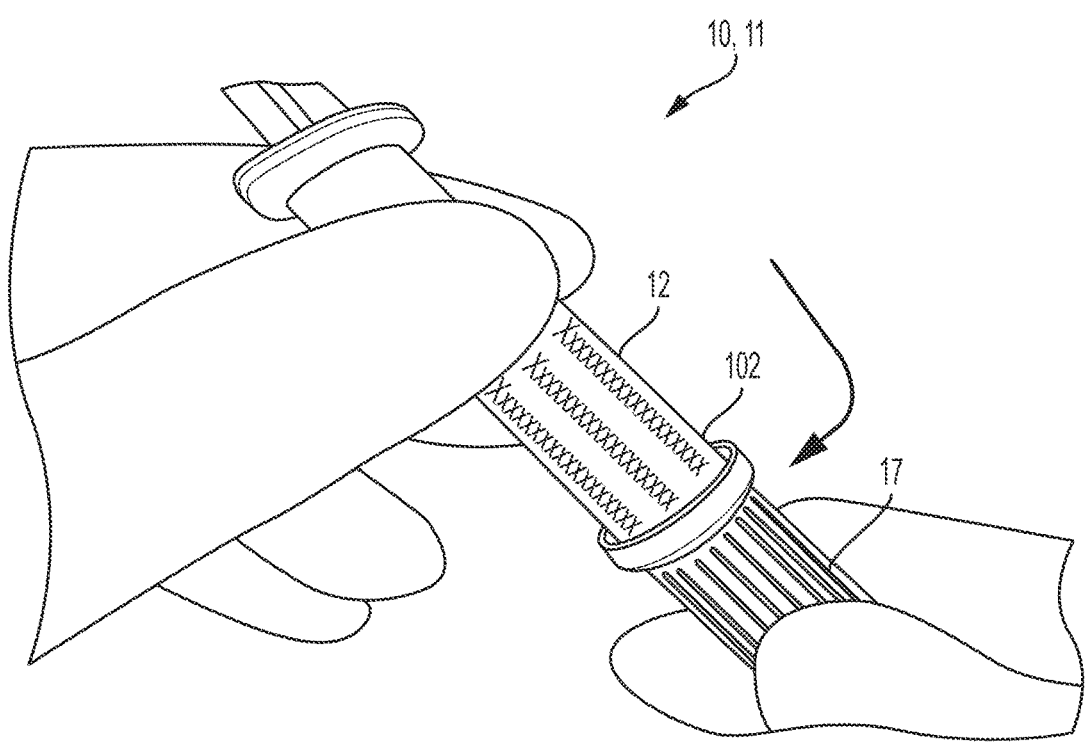
FIG. 37 is a perspective view of a sixth step of using a device of the present disclosure in accordance with an embodiment of the present invention.

Referring to FIG. 36, the cap 17 is removed from the tube 12 so that the syringe 13 is accessible. Next, referring to FIG. 37, the open end of the cap 17 can be placed on the closed distal end 102 of the tube 12.

Figure 38:
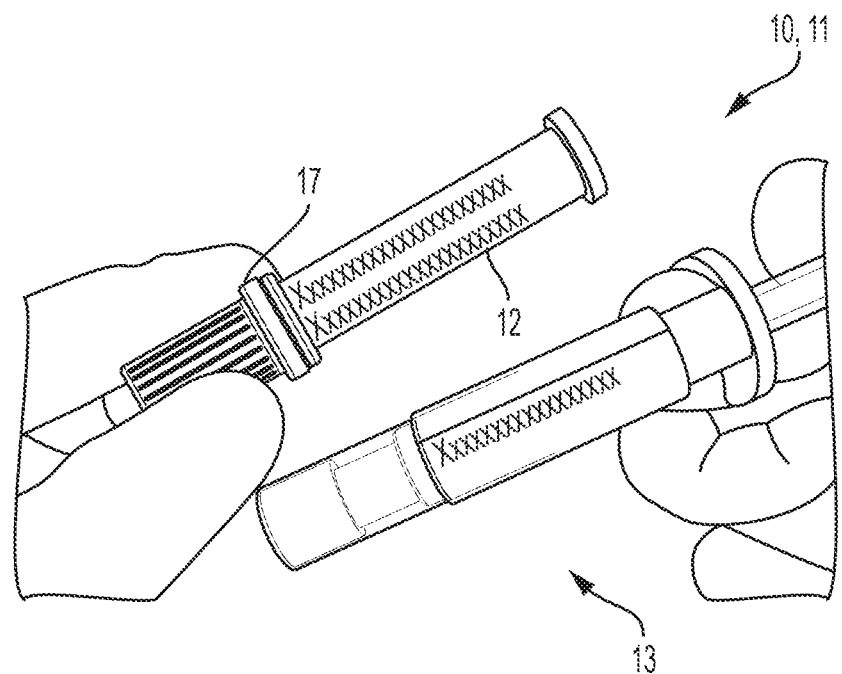
FIG. 38 is a perspective view of a seventh step of using a device of the present disclosure in accordance with an embodiment of the present invention.
Figure 39:
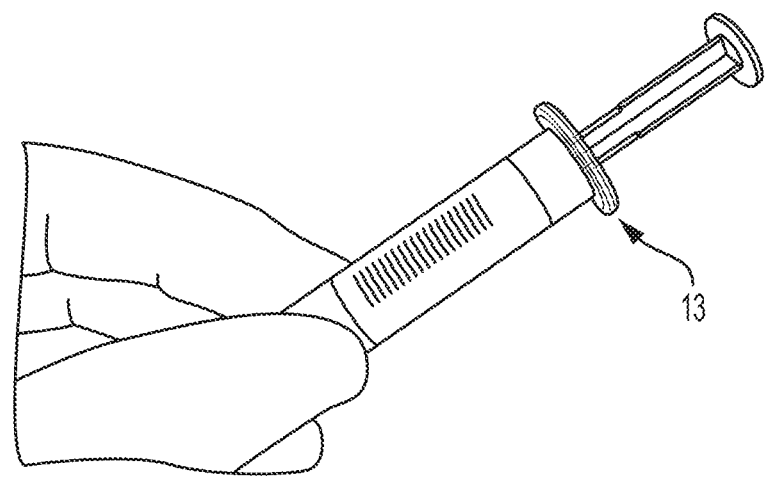
FIG. 39 is a perspective view of an eighth step of using a device of the present disclosure in accordance with an embodiment of the present invention.

Referring to FIG. 38, the syringe 13 can be removed from the packaging assembly 11. Next, the cap 17, the tube 12, and the tamper evident sleeve of the film 18 can be discarded. Before using the syringe 13, referring to FIG. 39, a visual inspection of the syringe 13 can be done by verifying important information.

Advantageously, after a proper inspection of the syringe 13 is performed, the syringe 13 is ready to be administered immediately upon removal of the packaging assembly 11.

Figure 40:
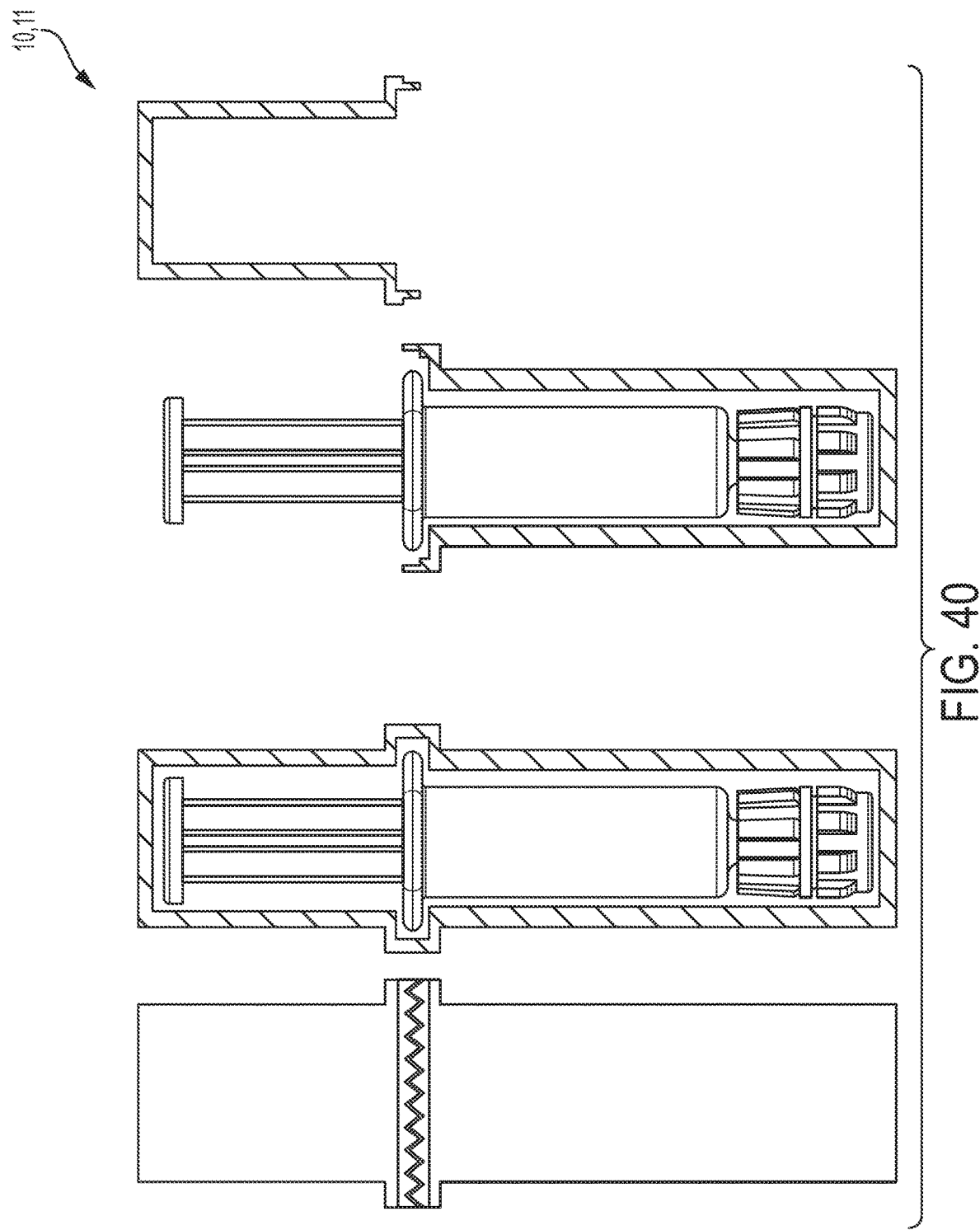
FIG. 40 are views of a syringe packaging system in accordance with another embodiment of the present invention.
Figure 41:
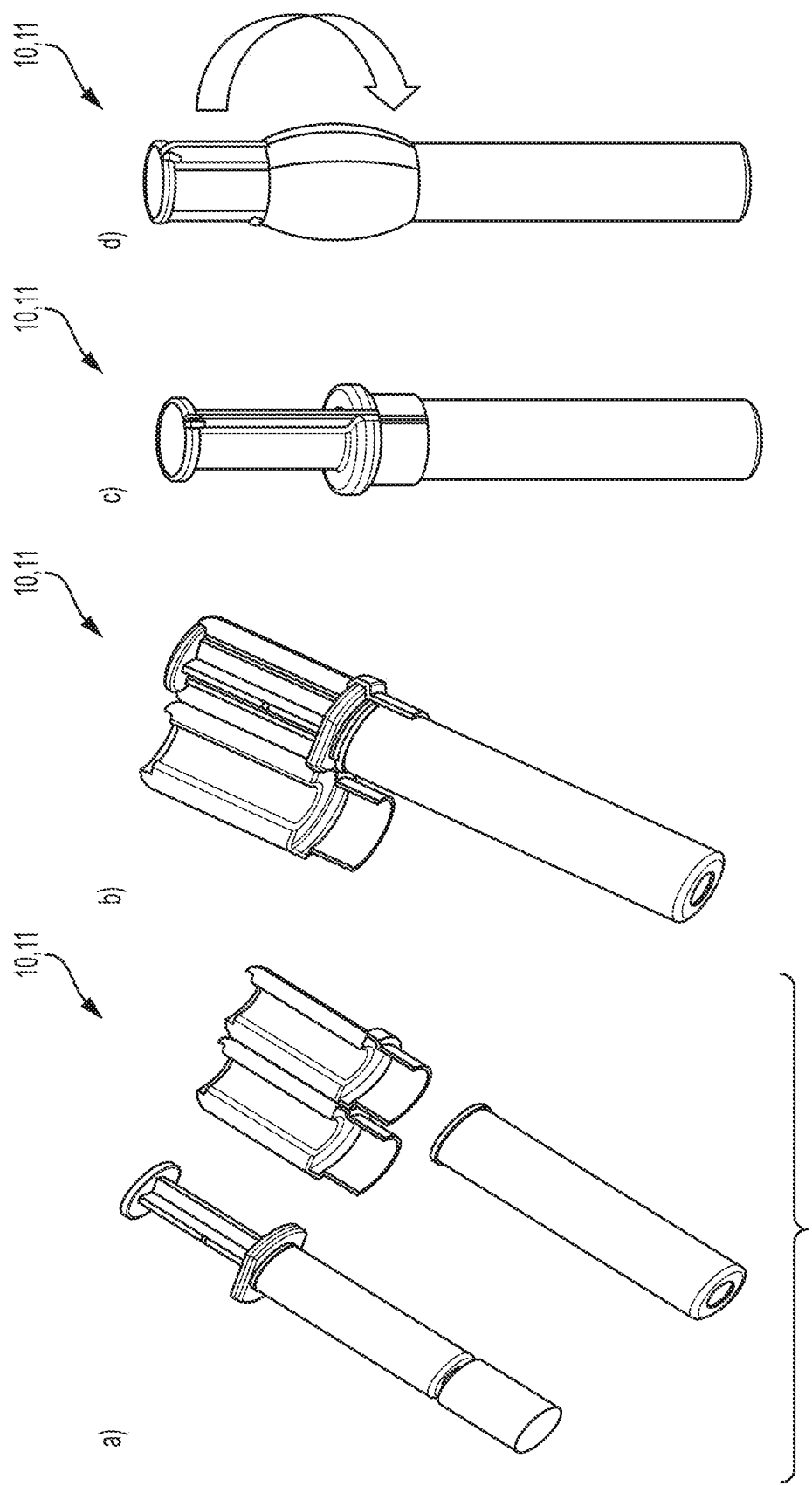
FIG. 41 are views of a syringe packaging system in accordance with another embodiment of the present invention.

FIGS. 40 and 41 illustrate other alternative exemplary embodiments of a packaging assembly 11 of the present disclosure.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A syringe packaging system, comprising:
    a pre-filled syringe including: (i) a syringe barrel having a proximal end, a distal end, and a sidewall extending therebetween and defining a chamber, the proximal end having a syringe barrel cut flange, and (ii) a plunger rod having a proximal end and a distal end; and
    a packaging member enclosing the pre-filled syringe, the packaging member including a tube having a proximal end and a distal end, the proximal end including a tube cut flange; and a cap for enclosing the syringe within the tube,
    wherein with the syringe contained within the tube, the syringe barrel cut flange is aligned with the tube cut flange.

2. The syringe packaging system of claim 1, wherein the syringe barrel cut flange includes a flat wall portion and an arcuate wall portion.

3. The syringe packaging system of claim 1, wherein the tube cut flange includes a flat wall portion and an arcuate wall portion.

4. The syringe packaging system of claim 1, wherein the cap comprises a first end and a second end, the second end including a cut skirt.

5. The syringe packaging system of claim 4, wherein the cut skirt includes a flat wall portion and an arcuate wall portion.

6. The syringe packaging system of claim 4, wherein, with the pre-filled syringe enclosed within the packaging member, the cut skirt of the cap surrounds the syringe barrel cut flange.

7. The syringe packaging system of claim 4, further comprising a film securable to a portion of the tube and a portion of the cap to connect the tube and the cap with the pre-filled syringe enclosed within the cap and the tube.

8. The syringe packaging system of claim 1, wherein the distal end of the tube is closed.

9. The syringe packaging system of claim 1, wherein the cap is engageable with the tube cut flange.

10. A syringe packaging system, comprising:
    a pre-filled syringe, comprising:
        a syringe barrel having a proximal end, a distal end, and a sidewall extending therebetween and defining a chamber, the proximal end having a syringe barrel cut flange;
        a fluid disposed within the chamber of the syringe barrel;
        a tip cap disposed at the distal end of the syringe barrel;
        a stopper slidably disposed within the chamber of the syringe barrel; and
        a plunger rod having a proximal end and a distal end engageable with a portion of the stopper; and
    a packaging member enclosing the pre-filled syringe, the packaging member comprising:
        a tube having a proximal end and a distal end, the proximal end including a tube cut flange;
        a cap for enclosing the tube, the cap having a first end and a second end, the second end including a cut skirt; and
        a film securable to a portion of the tube and a portion of the cap to connect the tube and the cap with the pre-filled syringe enclosed within the cap and the tube.

11. The syringe packaging system of claim 10, wherein the syringe barrel cut flange includes a flat wall portion and an arcuate wall portion.

12. The syringe packaging system of claim 10, wherein the tube cut flange includes a flat wall portion and an arcuate wall portion.

13. The syringe packaging system of claim 10, wherein the cut skirt includes a flat wall portion and an arcuate wall portion.

14. The syringe packaging system of claim 10, wherein, with the pre-filled syringe enclosed within the packaging member, the cut skirt of the cap surrounds the syringe barrel cut flange.

15. The syringe packaging system of claim 10, wherein, with the syringe barrel contained within the tube, the syringe barrel cut flange is aligned with the tube cut flange along a line extending from the respective proximal ends of the syringe barrel and the tube to the respective distal ends of the syringe barrel and the tube.

16. The syringe packaging system of claim 10, wherein the distal end of the tube is closed.

17. The syringe packaging system of claim 10, wherein the cap is engageable with the tube cut flange.

* * * * *